United States Patent [19]

Mihayashi et al.

[11] Patent Number: 4,734,357

[45] Date of Patent: Mar. 29, 1988

[54] SILVER HALIDE COLOR LIGHT SENSITIVE MATERIAL

[75] Inventors: Keiji Mihayashi; Hidetoshi Kobayashi; Isamu Itoh, all of Kanagawa, Japan

[73] Assignee: Fuji Photo Film Co., Ltd., Kanagawa, Japan

[21] Appl. No.: 6,351

[22] Filed: Jan. 14, 1987

Related U.S. Application Data

[63] Continuation of Ser. No. 583,925, Feb. 27, 1984, abandoned.

[30] Foreign Application Priority Data

Feb. 25, 1983 [JP] Japan ................................. 58-31610

[51] Int. Cl.$^4$ .............................................. G03C 1/40
[52] U.S. Cl. .................................... 430/376; 430/543; 430/955; 430/956; 430/957; 430/958; 430/505; 430/222; 430/598; 430/555; 430/553; 430/557; 430/558
[58] Field of Search ............... 430/376, 543, 955, 956, 430/957, 958, 505, 222, 598, 555, 553, 557, 558

[56] References Cited

U.S. PATENT DOCUMENTS

| | | | |
|---|---|---|---|
| 4,355,100 | 10/1982 | Sugita et al. | 430/957 |
| 4,414,308 | 11/1983 | Hamada | 430/957 |
| 4,518,682 | 5/1985 | Kobayashi | 430/543 |
| 4,628,024 | 12/1986 | Kobayashi et al. | 430/376 |

FOREIGN PATENT DOCUMENTS 2097140 10/1982 United Kingdom .

*Primary Examiner*—Won H. Louie
*Attorney, Agent, or Firm*—Sughrue, Mion, Zinn, Macpeak, and Seas

[57] ABSTRACT

A silver halide color light-sensitive material is described, which is increased in sensitivity, is adapted to form an image of high contrast, or is accelerated in development by incorporating a small amount of a specific compound which imagewise releases a foggant or a development accelerator. This compound is represented by the formula: Coup-(TIME)$_n$-FA (wherein Coup represents a coupler radical capable of undergoing a coupling reaction with an oxidized product of an aromatic primary amine developing agent; TIME represents a timing group which is eliminated from Coup by the coupling reaction and, thereafter, releases FA; n is 0 or 1; and FA represents a group which is eliminated from Coup in the coupling reaction when n is 0, whereas FA is released from TIME when n is 1. The FA has adsorption properties with respect to silver halide grains and also has a substantial fogging action with respect to the silver halide grains).

12 Claims, No Drawings

SILVER HALIDE COLOR LIGHT SENSITIVE MATERIAL

This is a continuation of application Ser. No. 583,925, filed Feb. 27, 1984, now abandoned.

FIELD OF THE INVENTION

The present invention relates to a silver halide color light-sensitive material, and more particularly, to a silver halide color light-sensitive material which is increased in sensitivity, is adapted to form an image of high contrast, or is accelerated in development by incorporating a small amount of a specific compound which imagewise releases a foggant or a development accelerator.

BACKGROUND OF THE INVENTION

It is well known that when a silver halide color light-sensitive material is exposed, an oxidized aromatic primary amine developer reacts with a dye-forming coupler, producing a dye image. In this method, color reproduction is usually carried out by the subtractive color process: i.e., dyes of cyan, magenta and yellow in complementary relation with red, green and blue, respectively, are formed. The reaction between the oxidized developing agent and the coupler occurs at an active site of the coupler.

A coupler having a hydrogen atom at the active site is a four equivalent coupler; i.e., it needs as an oxidizing agent 4 moles of silver halide with a developing nucleus in the formation of 1 mole of dye. On the other hand, a coupler having a releasing group as an anion at the active site is a two equivalent coupler; i.e., it requires only 2 moles of silver halide with a developing nucleus for the formation of 1 mole of dye. Therefore, when a two equivalent coupler is used, the amount of silver halide in a light-sensitive material and film thickness can be decreased compared with when the four equivalent coupler is used. Hence the use of the two equivalent coupler makes it possible to shorten the processing period of the light-sensitive material and further increases the sharpness of a color image formed. Furthermore, the coupling activity of the two equivalent coupler to the developing agent can be changed widely by suitably selecting the type of releasing group.

A two equivalent coupler releasing a compound capable of inhibiting development is called a "development inhibitor releasing coupler (DIR)". Since this coupler inhibits development in proportion to the amount of developed silver, it produces various effects, such as formation of fine grain images, control of gradation, and improvement of color reproductivity. Furthermore, the coupler can be used in the diffusion transfer process in view of its action on an adjacent layer.

By providing a releasing group containing a diffusing dye portion, the resulting coupler can be utilized in the diffusion transfer process in which the dye released is allowed to diffuse in an image-receiving layer and transferred thereto to form a dye image. Couplers of this type are called "diffusing dye-releasing couplers".

A certain kind of colored two equivalent coupler has the mask effect for color correction of a dye image. Couplers of this type are called "colored couplers".

As described above, the two equivalent coupler can be provided with various functions by suitably selecting the type of releasing group.

There are two general trends in the recent development of silver halide light-sensitive materials, particularly light-sensitive materials for cameras; one is high sensitization exemplified by a film of ASA 400, and the other is an improvement in image quality so as to cope with miniaturization of films. In connection with the former high sensitization, various techniques have heretofore been studied, including a method of increasing the grain size of silver halide, a method of increasing the activity of couplers, and acceleration of development.

The sensitivity seems to have reached the uppermost limit as described in G. C. Farnell & J. B. Chanter, *J. Photogr. Sci.*, Vol. 9, page 75 (1961) and thus no further increase in sensitivity can be expected even by increasing the grain size of the silver halide. Furthermore, various problems such as reduction of graininess are involved in increasing the grain size of silver halide. Extensive investigations have heretofore been made to increase the activity of couplers. This activation, however, cannot be achieved to an extent sufficient to contribute to the increase of sensitivity. On the contrary, it has a disadvantage of reducing the graininess. In connection with the acceleration of development, incorporation of various development accelerators such as hydrazines in an emulsion layer or a developer has heretofore been investigated mainly for black and white light-sensitive materials. However, addition of such development accelerators often results in an increase of fog and reduction of graininess, and is not suitable for practical use.

In view of the problems as described above, a coupler releasing imagewise a development accelerator or a foggant has been proposed. For example, U.S. Pat. Nos. 3,214,377, 3,253,924, and Japanese Patent Application (OPI) No. 17437/76 (the term "OPI" as used herein means a 'published unexamined Japanese patent application") discloses a thiocyanic acid ion-releasing coupler which accelerates solution physical development. In addition, Japanese Patent Application (OPI) No. 150845/82 discloses a coupler releasing acylhydrazine, and Japanese Patent Application (OPI) No. 138636/82 discloses couplers releasing developing agents such as hydroquinone and aminophenols.

The above-described releasing groups, however, are inferior in the development acceleration or fogging action. Therefore, the development acceleration or fogging effect is difficult to obtain unless the couplers releasing such groups are used in large amounts. Furthermore, even if they are used in large amounts, the effect obtained is very small. Moreover, when the couplers are incorporated in a certain light-sensitive layer, they diffuse in another layer because of high diffusability of the releasing groups, causing the acceleration of development or fogging in the different layer. This is not preferred for color reproduction because of color mixing and further reduces the graininess.

SUMMARY OF THE INVENTION

An object of the invention is to provide a light-sensitive material which is of high sensitivity and provides an image of reduced fog and good color reproductivity.

Another object of the invention is to provide a light-sensitive material which forms an image of high contrast.

Another object of the invention is to provide a light-sensitive material which is improved in developing properties.

Another object of the invention is to provide a light-sensitive material which provides high color density.

Another object of the invention is to provide a light-sensitive material in which the amount of silver used is reduced.

It has been found that the objects are attained by incorporating a specific compound represented by the general formula (I) as described hereinafter in a light-sensitive emulsion layer.

The present invention relates to a silver halide color light-sensitive material comprising a support and at least one light-sensitive silver halide emulsion layer on the support, wherein a compound represented by the general formula (I):

Coup-(TIME)$_n$-FA  (I)

(all the symbols are described hereinafter in detail) is incorporated in the light-sensitive silver halide emulsion layer in an amount of not more than 1 mol% of all the couplers contained in said emulsion layer and other emulsion layers sensitive to the same color as said emulsion layer.

DETAILED DESCRIPTION OF THE INVENTION

The compound to be incorporated in the silver halide color light-sensitive material of the invention is represented by the general formula (I):

Coup-(TIME)$_n$-FA  (I)

wherein Coup represents a coupler radical capable of undergoing a coupling reaction with an oxidized product of an aromatic primary amine developing agent; TIME represents a timing group which is eliminated from Coup by the coupling reaction and, thereafter, releases FA; n is 0 or 1; and FA represents a group which is eliminated from Coup in the coupling reaction when n is 0, whereas FA is released from TIME when n is 1, and which shows adsorption properties with respect to silver halide grains and also has a substantial fogging action with respect to the silver halide grains.

The term "group having a substantial fogging action" as used herein means that the group produces a determinable amount of fog when development is performed in the presence thereof.

The coupler radicals represented by the symbol Coup include:

cyan coupler radicals such as a phenol coupler and a naphthol coupler;

magenta coupler radicals such as a 5-pyrazolone coupler, a pyrazolobenzimidazole coupler, a pyrazolotriazole coupler, a cyanoacetylcumarone coupler, an open chain acylacetonitrile coupler, and an imidazolone coupler;

yellow coupler radicals such as a benzoylacetoanilide coupler, a pivaloylacetoanilide coupler, and a malondianilide coupler; and colorless coupler radicals such as open chain or cyclic active methylene compounds (e.g., indanone, cyclopentanone, malonic acid diesters, imidazolinone, oxazolidine, and thiazolinone).

Of the coupler radicals represented by the symbol Coup, the groups represented by the general formulae (II) to (X) as described hereinafter are preferably used in the present invention.

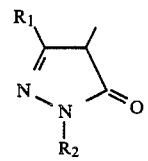
(II)

wherein $R_1$ is an acylamido group, an anilino group, or a ureido group, and $R_2$ is a phenyl group which may be substituted by at least one halogen atom, alkyl group, alkoxy group, or cyano group.

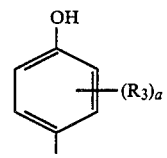
(III)

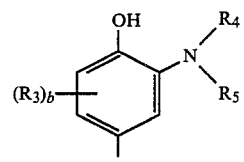
(IV)

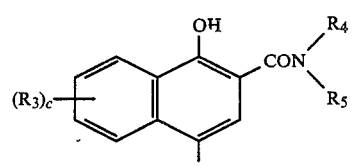
(V)

In the above formulae, $R_3$ is a halogen atom, an acylamido group, or an aliphatic radical, $R_4$ and $R_5$ are each an aliphatic radical, an aromatic radical, or a heterocyclic radical and one of $R_4$ and $R_5$ may be a hydrogen atom, a is an integer of 1 to 4, b is an integer of 0 to 3, and c is an integer of 0 to 5.

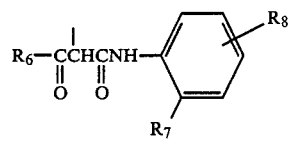
(VI)

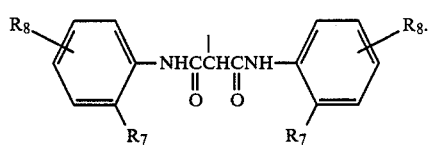
(VII)

In the above formulae, $R_6$ is a tert-alkyl group or an aromatic radical, $R_7$ is a hydrogen atom, a halogen atom, or an alkoxy group, and $R_8$ is an acylamido group, an aliphatic radical, an alkoxycarbonyl group, a sulfamoyl group, a carbamoyl group, an alkoxy group, a halogen atom, or a sulfonamido group.

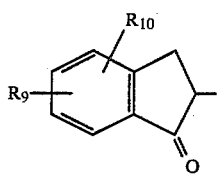
(VIII)

wherein $R_9$ is an aliphatic radical, an alkoxy group, a mercapto group, an alkylthio group, an acylamido group, an alkoxycarbonyl group, a sulfonamido group, a carbamoyl group, a sulfamoyl group, an alkoxysulfonyl group, an aryloxysulfonyl group, an acyl group, a diacylamino group, an alkylsulfonyl group, or an arylsulfonyl group, and $R_{10}$ is a hydrogen atom, a halogen atom, an alkoxy group, an acyl group, a nitro group, an alkylsulfonyl group, or an arylsulfonyl group.

Enol esters of indanone can also be used in the present invention.

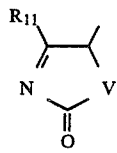
(IX)

wherein $R_{11}$ is an aliphatic radical or an aromatic radical, and V is an oxygen atom, a sulfur atom, or a nitrogen atom.

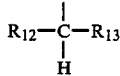
(X)

wherein $R_{12}$ and $R_{13}$ are each

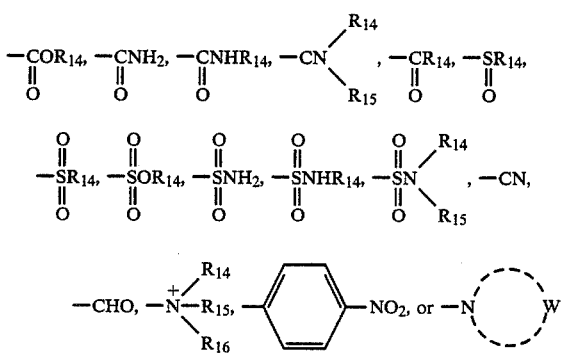

(wherein $R_{14}$, $R_{15}$ and $R_{16}$ are each a hydrogen atom, an aliphatic radical, an aromatic radical, or a heterocyclic ring, W is a non-metallic atom group necessary for forming a 5 or 6-membered ring in combination with a nitrogen atom, and $R_{12}$ and $R_{13}$ may form a 6-membered ring in combination with the necessary non-metallic atom group).

Examples of the timing group represented by the symbol TIME include:

a group, as described in U.S. Pat. No. 4,248,962 and Japanese Patent Application (OPI) No. 56837/82, which is eliminated from Coup by the coupling reaction and, thereafter, releases FA in the intramolecular displacement reaction;

a group, as described in British Pat. No. 2072363A, Japanese Patent Application (OPI) Nos. 154234/82, and 188035/82, which releases FA by the movement of electrons through a conjugated system; and a coupling component as described in Japanese Patent Application (OPI) No. 111536/82, which is capable of releasing FA when undergoing a coupling reaction with an oxidized product of an aromatic primary amine developing agent. These reactions may occur during one-stage or during multi-stages.

The following descriptions relating to (OPI) 56837/82 and (OPI) 188035/82 are inserted based on translations of essential portions of each of them.

The timing group expressed by TIME in Japanese Patent Application (OPI) No. 56837/82 means a group represented by an

portion in the following formula:

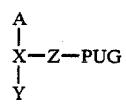

In the above formula, A represents a component capable of reacting with the oxidation product of a color-developing agent, PUG represents a photographically useful group, Y represents a nucleophilic group precursor which may be connected with X to form a ring and Z represents an electrophilic group. X is a group by which Y is three-dimensionally connected with Z and is connected with A at a position capable of being substituted with the oxidation product of the color-developing agent. After the bond between A and X is cleaved, Y is changed to a nucleophilic group which causes a displacement reaction with a ring closure with Z whereby PUG is released.

The groups represented by X, Y and Z in the above-described formula are groups capable of releasing the photographically useful group with controllable timing.

To explain the above-described compounds in view of their basic behavior, the A component can include any components capable of releasing an

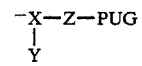

group upon reaction with the oxidation product of the color developing agent, examples of which components include conventional couplers capable of forming a colored substance upon reaction with the oxidation product of the color-developing agent and compounds capable of forming a colorless substance upon reaction with the oxidation product of the color developing agent. The A component need not be stabilized (have a ballast group), but it may be stabilized with an oil-soluble group or an aliphatic group. An

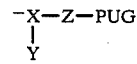

group is connected with the A component at a position where the A component reacts with the oxidation product of the color-developing agent. Therefore, after the compound represented by the above-described formula is reacted with the oxidation product of the color-developing agent, the

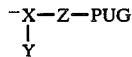

group is released. On the other hand, a part of the released

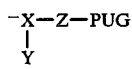

group is present as an

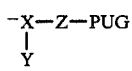

group through the conjugated system in X because of the occurrence of the delocalization of electrons. Consequently, Y which is a nucleophilic precursor is changed to a nucleophilic group which can cause an intramolecular nucleophilic displacement reaction with Z which is an electrophilic group, whereby PUG is ultimately released. Thus X is a group by which Y and Z are related with the three-dimensional position.

Further, the timing group represented by TIME in Japanese Patent Application (OPI) No. 188035/82 means a group represented by an

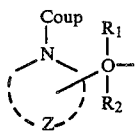

portion in the following formula:

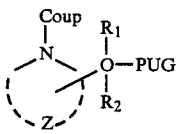

In the above formula, Coup represents a coupling component capable of coupling with the oxidation product of a color-developing agent, $R_1$ and $R_2$ each represents a hydrogen atom, an alkyl group or an aryl group, Z represents a structural element capable of forming a 5-membered heterocyclic ring (inclusive of one forming a condensed ring), and Coup is connected with the heterocyclic ring at a position capable of being substituted with the oxidation product of the color-developing agent. PUG represents a photographically useful group capable of being released after the heterocyclic ring is released from Coup.

British Pat. No. 2,072,363 A discloses that the compounds which are preferable for use are represented by the formula as follows:

A-TIME-PUG     (1)

where "A" is the coupler group capable of coupling reaction with the oxidized color developing agent, "TIME" the timing group and "PUG" the photographically useful group.

In the above formula, any compound may be used for the coupler group A insofar as it can react with the oxidized color developing agent to release the group -TIME-PUG. Examples of the coupler group include one which will form a colored product or a colorless product on coupling reaction with the oxidized color developing agent. The coupler group A may have no ballasting group or may be ballasted with an oil soluble or aliphatic group or groups. The group -TIME-PUG is attached to the component A at the coupling site, which is capable of coupling reaction with the oxidized color developing agent. The timing group joining the PUG and the component A may be any organic group such that it can be cleaved from the PUG as a result of an electron transfer along a conjugated system toward PUG after the group -TIME-PUG is cleaved from the component A.

In British Pat. No. 2,072,363 A, the term "conjugated system" refers to the form of bonding well known in chemistry, namely the one in which a single bond and a double or triple bond appear alternatively in the chemical formula. Accordingly, it is assumed that the lone pair electron on the fragment -TIME-PUG cleaved from the component A is transferred along a conjugated system to ultimately break the bond between the TIME and PUG.

Examples of the timing group are formulated in the following formula:

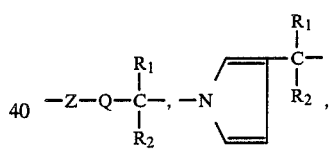

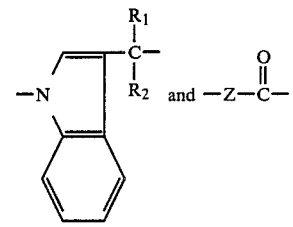

wherein the left hand side is attached to the coupler group, Z is O, S, or

$R_1$, $R_2$ and $R_3$ are individually a hydrogen atom, alkyl or aryl group, Q is 1,2- or 1,4-phenylene or naphthylene group. The phenylene or napthylene may have a substituent such as halogen atom, alkyl, alkoxy, —CN, —NO₂, —NHCOR or —COOR wherein R is alkyl.

In case the TIME group forms quinomethide or naphthoquinomethide on the final cleavage, the compound includes one represented by the following general formula:

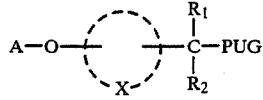   (2)

where "A" and "PUG" are the same as defined in the general formula (1) of British Pat. No. 2,072,363 A while "X" represents atoms necessary to complete a substituted or nonsubstituted benzene or napthalene nucleus and "$R_1$" and "$R_2$" individually represent a hydrogen atom, alkyl group or aryl group, with the group

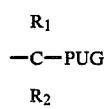

being joined at the para or ortho position relative to the oxygen atom.

The compound as represented by the above general formula (2) of British Pat. No. 2,072,363 A is cleaved as it reacts with the oxidized color developing agent, first forming a compound as represented by the following general formula (3), which is then recleaved through an electron transfer along the conjugated system to form a compound as represented by the following general formula (4) while releasing the PUG:

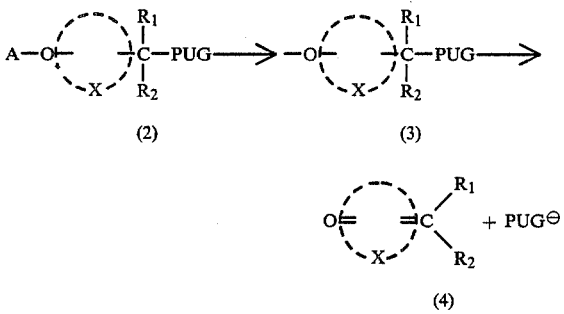

The above compound (4) is called either quinonemethide or naphthoquinonemethide.

Next, as a compound of British Pat. No. 2,072,363 A, a compound comprising a timing group which will ultimately form a quinomethide compound and phenylmercaptotetrazole as the PUG is selected to illustrate the process diagrammatically:

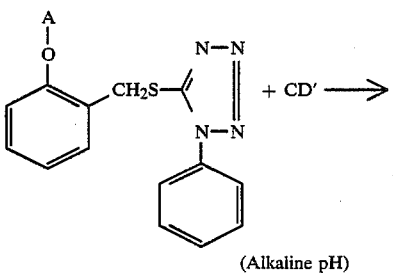

(Alkaline pH)

-continued

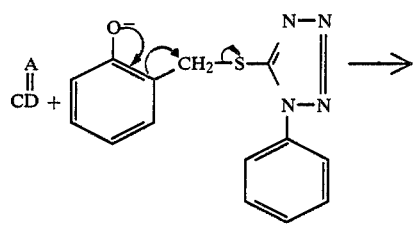

(Development inhibitor)

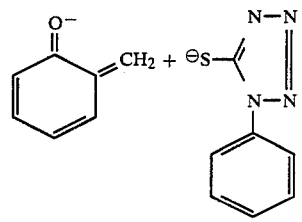

(Orthoquinonemethide)

where "CD" represents the oxidized color developing agent.

In the above diagram, upon the coupling reaction, the compound cleaves to release the timing group bonded to the photographically useful group (development inhibitor in this case), which is then recleaved by an electron transfer along the conjugated system as indicated by arrows to form orthoquinomethide while releasing the development inhibitor.

Further, the process is again illustrated diagrammatically below for a compound that uses a timing group other than the one used above as another example:

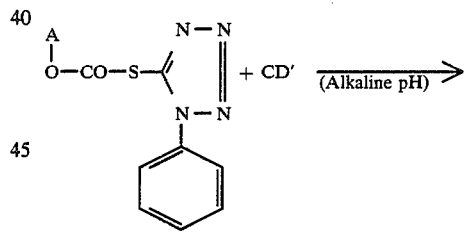

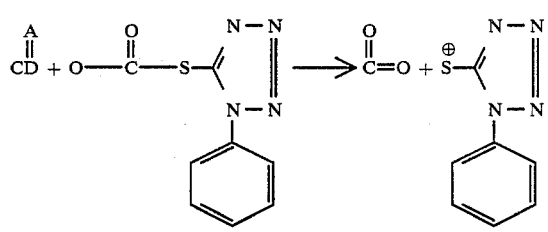

(Development inhibitor)

where "A" and "CD" are the same as defined previously. Also in this case, in the fragment that is released from the compound after its reaction with CD' a lone pair electron located on the oxygen atom is conjugated with the carbonyl π electrons.

The coupler of Japanese Patent Application (OPI) No. 111536/82 has the following structure:

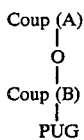

wherein Coup (A) represents a coupling component (A) and Coup (B) a coupling component (B), Coup (A) being bonded to the oxygen atom O at the position capable of forming a colored or a colorless compound through coupling with an oxidized form of a color forming developing agent, Coup (B) being bonded to the oxygen atom in the form such that it can be made for the first time capable of coupling with an oxide of a color forming developing agent by being released from Coup (A) upon coupling of Coup (A), and PUG being bonded at the position capable of coupling with an oxide of a color forming developing agent of Coup (B) and in the form such that it can be released from Coup (B) by said coupling.

The mechanism of action of the coupler for photography represented by the above formula is schematically illustrated below:

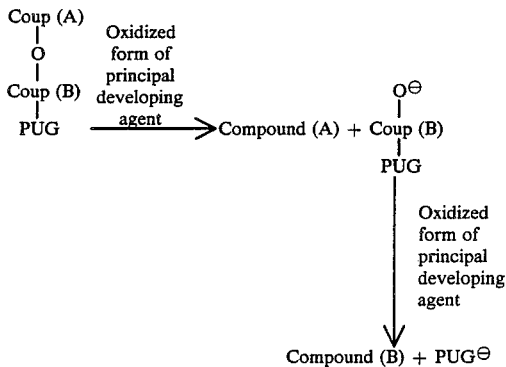

wherein Coup (A), Coup (B) and PUG are the same as defined in the above formula; Compound (A) and Compound (B) are products formed by coupling of Coup (A) and Coup (B), respectively, with an oxidized form of a developing agent.

As the coupling component (A) and the coupling component (B) of the present invention, there may generally be employed residues of yellow, cyan and magenta couplers conventionally used for silver halide photographic photosensitive materials. Among them, there are included those which can form colorless compounds through coupling with an oxidized form of a color forming developing agent and also those which can form colored compounds. Examples of those capable of forming colorless compounds through coupling are acetophenone derivative residues and indanone derivative residues, while those capable of forming colored compounds through coupling may include various residues of couplers as enumerated below.

As yellow couplers are concerned, there may be mentioned benzoyl acetoanilide type yellow couplers or pivaaloyl acetanilide type yellow couplers. As for magenta couplers, there are various magenta couplers such as pyrazolone type magenta couplers and indazolone type magenta couplers.

Further, in case of cyan couplers, there are naphthol type of phenol type couplers.

As a photographically useful group PUG, there may be employed any group which can cause a photographically advantageous effect in a photographic element.

More preferably, in the above formula, the moiety excluding Coup (A) may be a diffusible compound residue.

Japanese Patent Application (OPI) No. 154234/82 discloses a compound used in silver halide photographic material having the following structure:

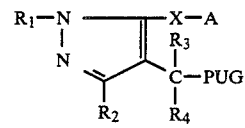

wherein A represents a group being capable of leaving under photographic treatment, X represents —O—, —S— or

(wherein $R_5$ represents a hydrogen atom, an alkyl group, an aryl group, an acyl group or a sulfonyl group) and can form a condensed ring together with $R_1$, $R_1$ represents a hydrogen atom, an alkyl group, an aryl group, an acyl group, a sulfonyl group, an alkoxy group, an amino group, a carbamide, a sulfonamide, a carboxyl group, an alkoxycarbonyl group, a carbamoyl, a cyano group or a halogonized alkyl group, $R_3$ and $R_4$ represent a hydrogen atom, alkyl group or an aryl group, PUG represents a photographically useful group connecting with a carbon atom substituted at the fourth position of pyrazole ring. PUG contains, for example, groups for silver halide-solving agent, a hardener, a fogging agent, a developer, a development accelerator, a development inhibitor, but a group for a development inhibitor is most preferable.

In the general formula (I), as described above, FA represents a group which is eliminated from Coup in the coupling reaction when n is 0, whereas FA is released from TIME when n is 1, and which shows adsorption properties with respect to silver halide grains and also has a substantial fogging action on silver halide.

Examples of FA include a group represented by the formula: AD-(L)$_m$-X, and a group having the functions or structures of AD and X at the same time in one molecule. In the above formula, AD is a group capable of being adsorbed onto silver halide grains, L is a divalent bonding group, X is a reducing group, or a group capable of forming silver sulfide at the time of development, and m is 0 or 1. When FA is a group represented by the formula: AD-(L)$_m$-X, it may be linked to TIME at any point of AD-(L)$_m$-X. In the present invention, it is preferred to use, as FA, a group which has both the functions of AD and X as described above in one molecule. AD may be bonded directly to a carbon atom at the coupling site and may be bonded to the coupling carbon as long as either L or X can be eliminated by the coupling reaction. Furthermore, there may exist a so-called 2 equivalent releasing group between the coupling carbon and AD.

Typical examples of FA groups include an alkoxy group (e.g., a methoxy group), an aryloxy group (e.g., a phenoxy group), an alkylthio group (e.g., an ethylthio group), an arylthio group (e.g., a phenylthio group), a heterocyclic oxy group (e.g., tetrazolyloxy), a heterocyclic thio group (e.g., pyridylthio), a heterocyclic group (e.g., a hydantoinyl group, a pyrazolyl group, a triazolyl group, and a benzotriazolyl group), and the like. In addition, the groups described in British Patent No. 2,011,391 A can also be used as FA.

Groups capable of being absorbed on to silver halide, as represented by AD in the above formula, include:

nitrogen-containing heterocyclic rings containing therein a dissociative hydrogen atom (e.g., pyrrole, imidazole, pyrazole, triazole, tetrazole, benzimidazole, benzopyrazole, benzotriazole, uracyl, tetrazaindene, imidazotetrazole, pyrazolotriazole, and pentazaindene);

heterocyclic rings containing at least one nitrogen atom and other hetero atom (e.g., an oxygen atom, a sulfur atom, and a selenium atom) in the ring (e.g., oxazole, thiazole, thiazoline, thiazolidine, thidiazole, benzothiazole, and benzoxazole);

heterocyclic rings containing a mercapto group (e.g., 2-mercaptobenzothiazole, 2-mercaptopyrimidine, 2-mercaptobenzoxazole, and 1-phenyl-5-mercaptotetrazole);

quaternary salts (e.g., tertiary-amines, pyridine, quinoline, benzothiazole, benzimidazole, and benzoxazole);

thiophenols and alkylthiols (e.g., cysteine); and compounds having a partial structure:

(e.g., thiourea, dithiocarbamate, thioamide, rhodanine, thiazolidinethione, thiohydantoin, and thiobarbituric acid).

Useful divalent bonding groups represented by L in the above formula include commonly used divalent bonding groups such as alkylene, alkenylene, phenylene, naphthylene, —O—, —S—, —SO—, —SO₂—, —N=N—, carbonylamido, thioamido, sulfonamido, ureido, thioureido, and heterocyclic rings.

Useful groups represented by X in the above formula include reducing compounds (e.g., hydrazine, hydrazide, hydrazone, hydroquinone, catechol, p-aminophenol, p-phenylenediamine, 1-phenyl-3-pyrazolizinone, enamine, aldehyde, polyamine, acetylene, aminoborane, quaternary salts such as tetrazolium salt and ethylenebispyridinium salt, and carbazinic acid) and compounds capable of forming silver sulfide at the time of development (those containing a group:

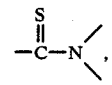

such as thiourea, thioamide, dithiocarbamate, rhodanine, thiohydantoin, and thiazolidinethione).

Of the groups represented by X, the compounds capable of forming silver sulfide at the time of development show adsorption properties with respect to silver halide grains by themselves and thus can function as an adsorbent group AD.

FA is an adsorption site for silver halide grains; for example, it is a nitrogen atom in benzotriazole, or a sulfur atom in 1-phenyl-5-mercaptotetrazole. It may be bonded to TIME or Coup, but is not always required to be bonded thereto. In this case, it is preferred that a hydrogen atom be bonded to the adsorption site, or the adsorption site be blocked with a group which is hydrolyzable in a developer (e.g., an acetyl group, a benzoyl group, and a methanesulfonyl group) or a group which can be eliminated during development (e.g., 2-cyanoethyl group, and a 2-methanesulfonylethyl group).

Typical examples of AD are shown below.

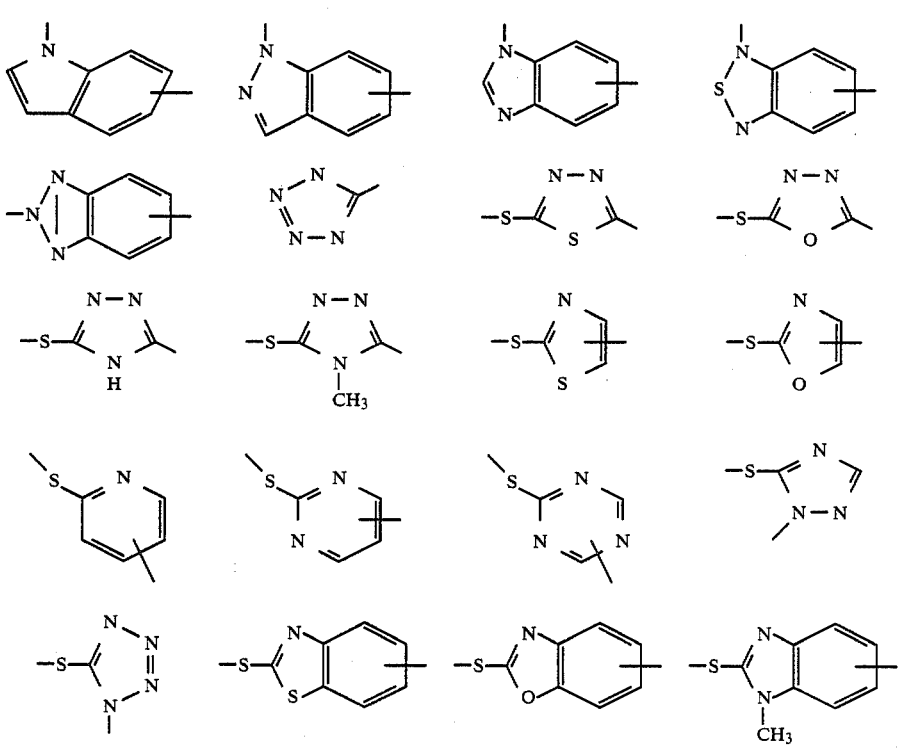

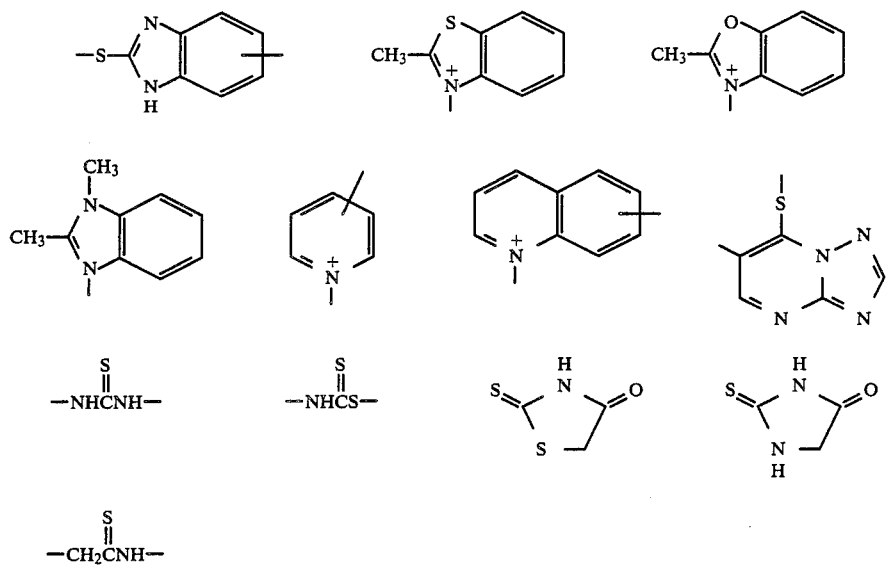
Typical examples of L are shown below.
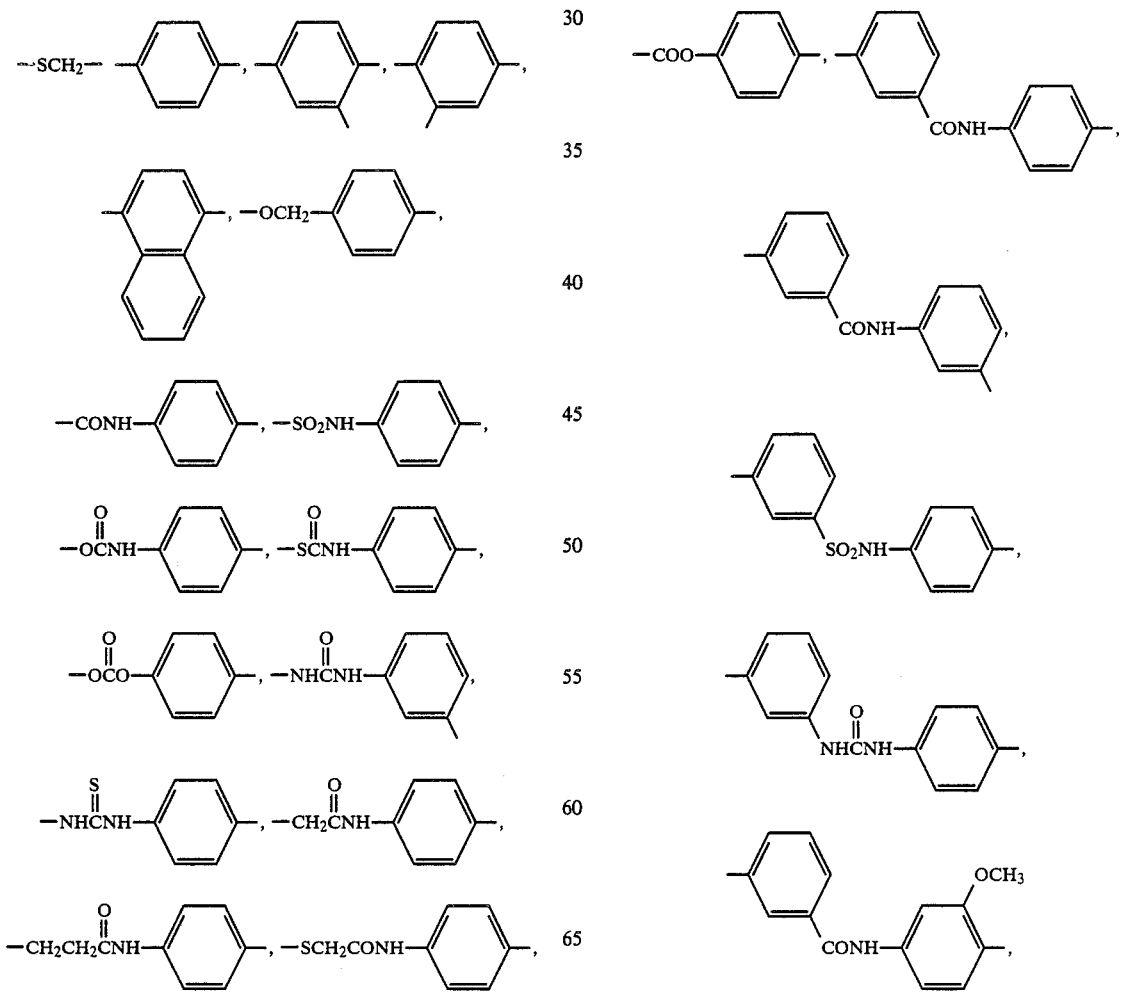

-continued
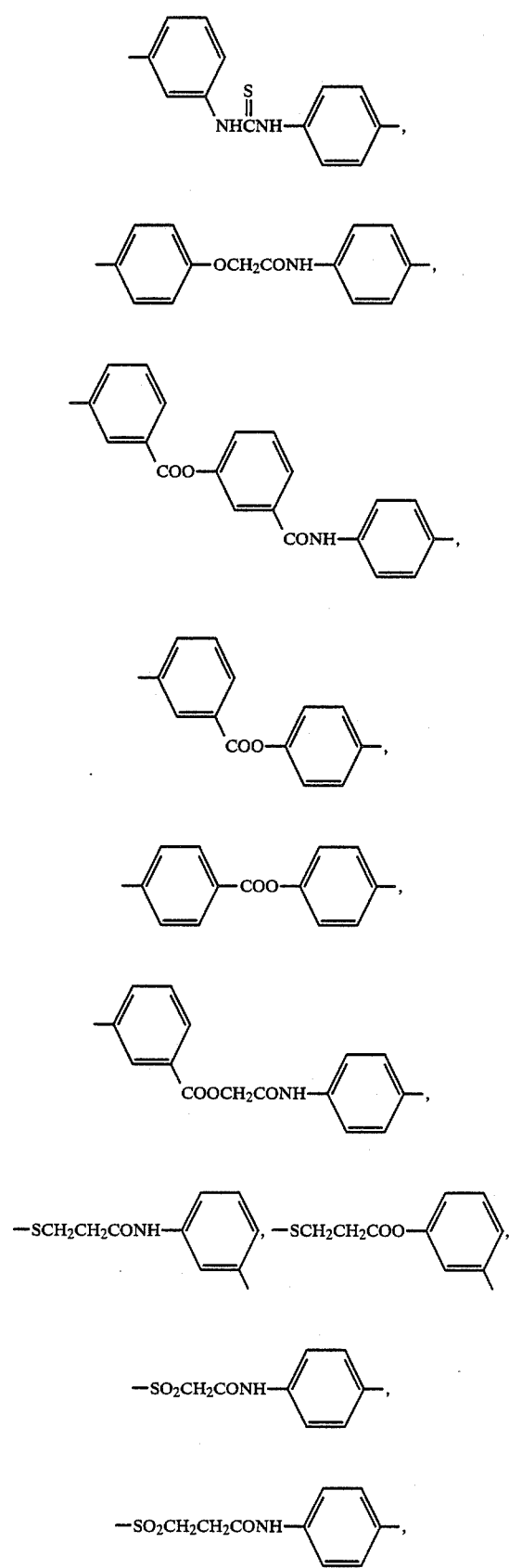
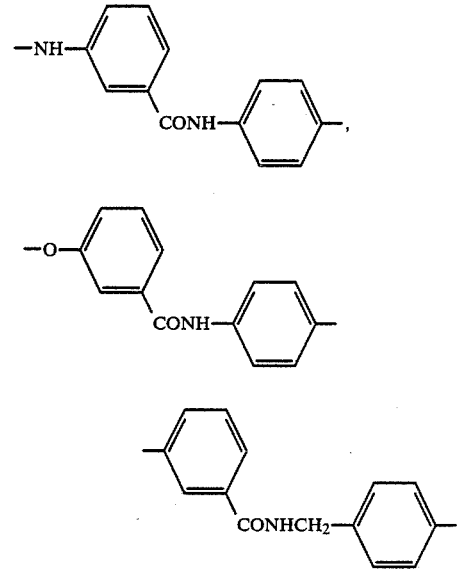
Typical examples of X are shown below.
—NHNHCHO, —NHNHCOCH$_3$, —NHNHSO$_2$CH$_3$,
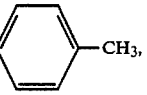
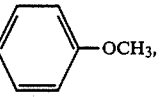
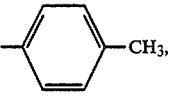
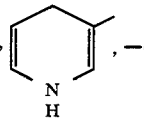
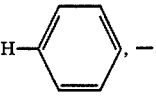
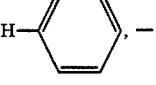
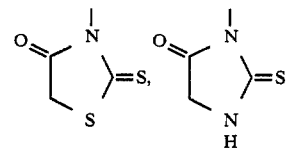
Preferred examples of FA in the general formula (I) are shown below.

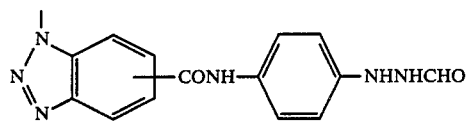
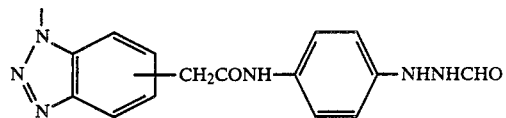
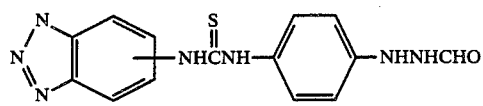
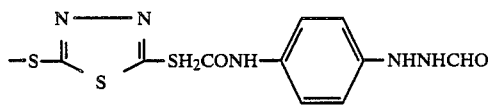
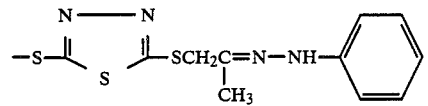
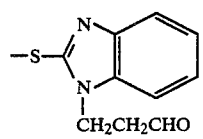
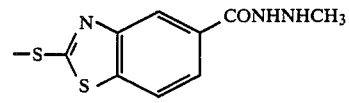
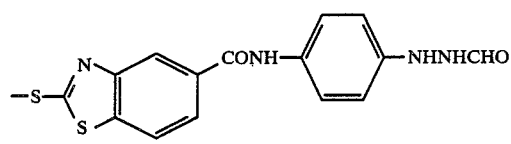
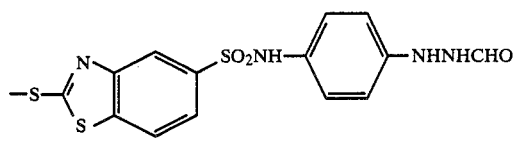
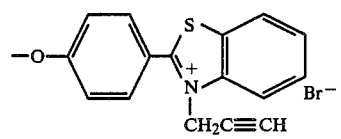
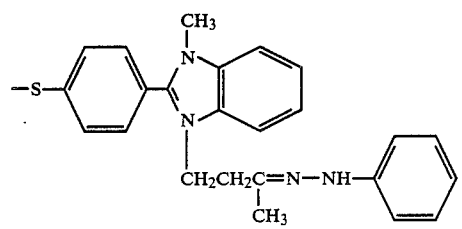
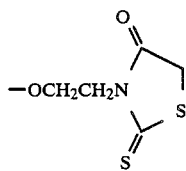
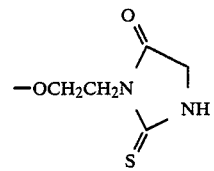
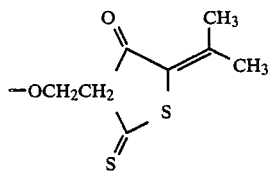
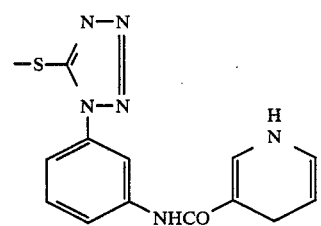
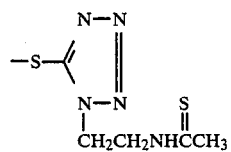
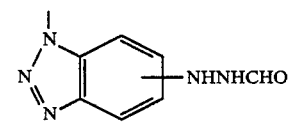
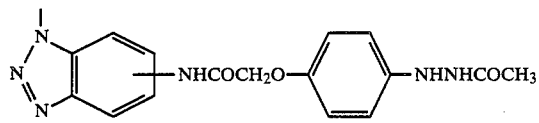
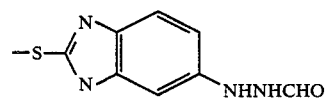

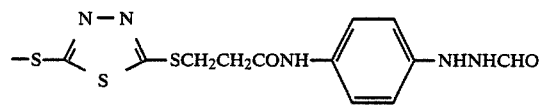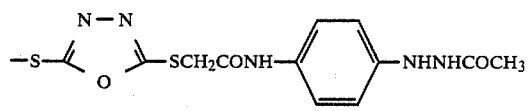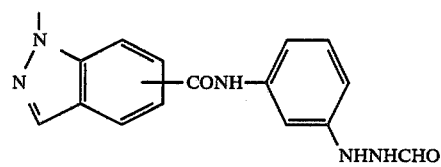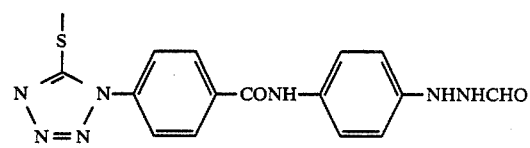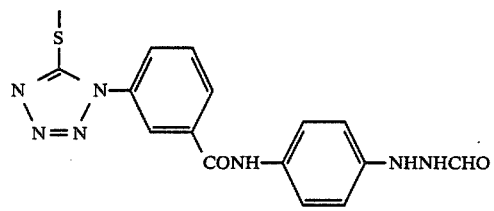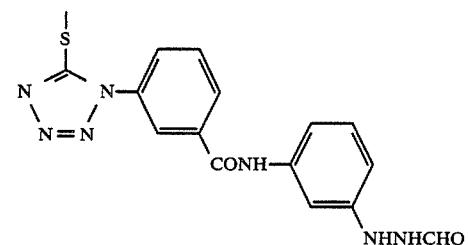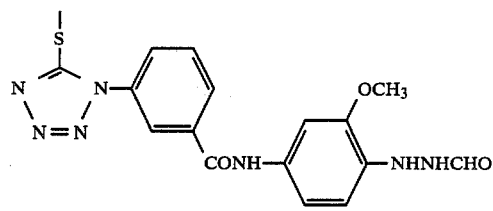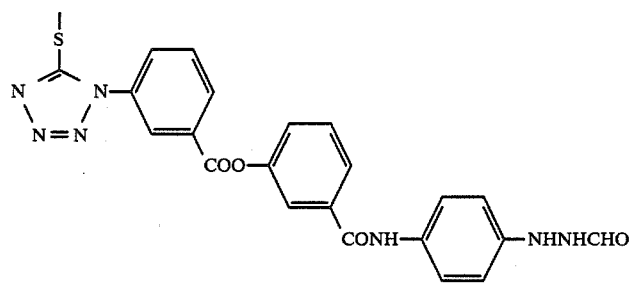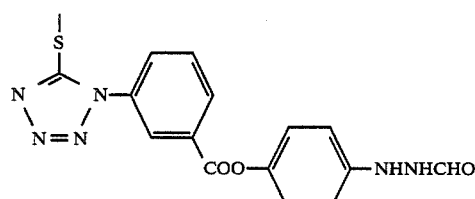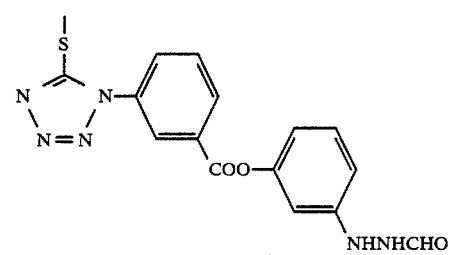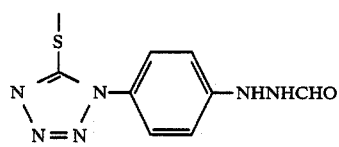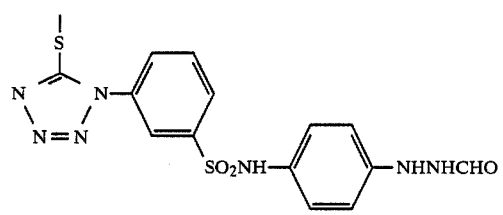

-continued
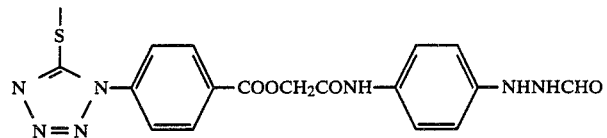
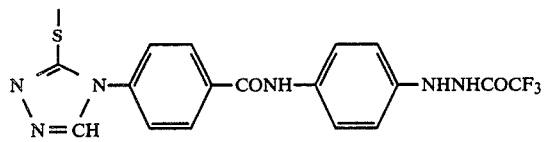
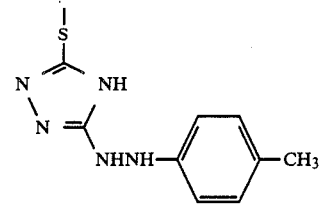
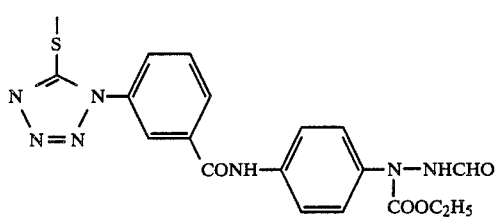
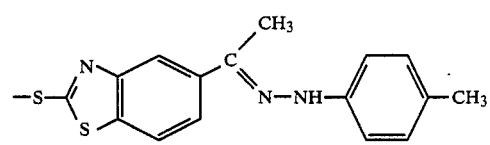
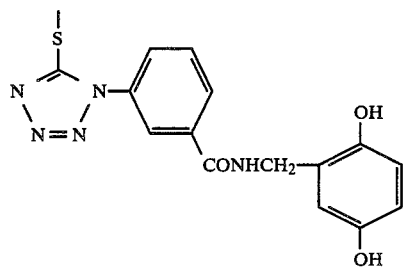
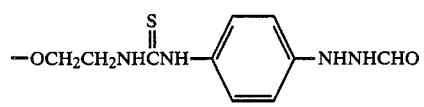
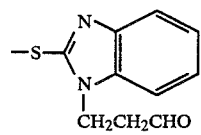
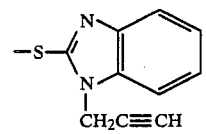
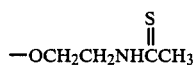
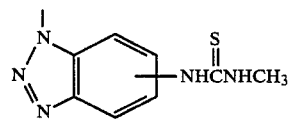
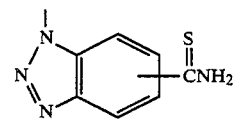
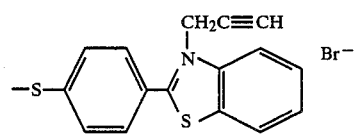
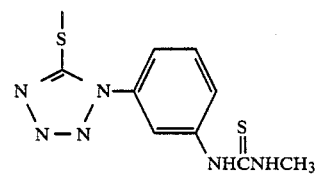

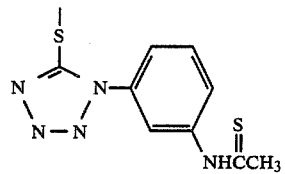
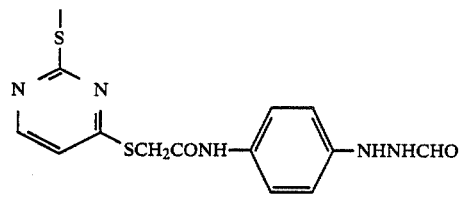
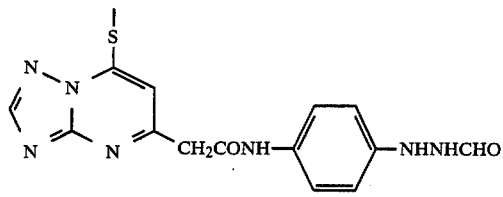
Preferred examples of the compounds represented by the general formula (I) are shown below.
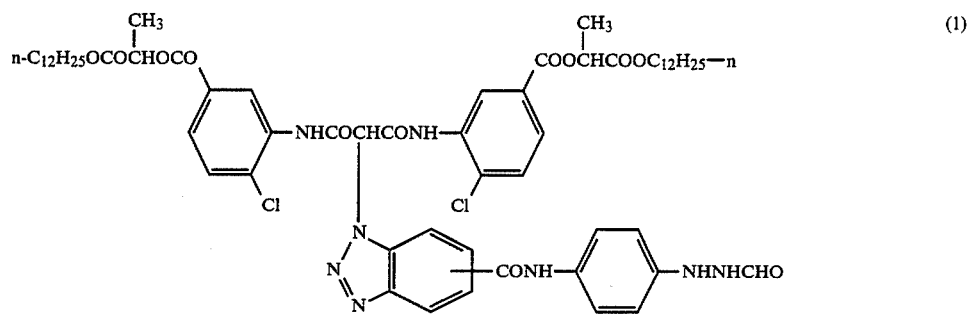
(1)
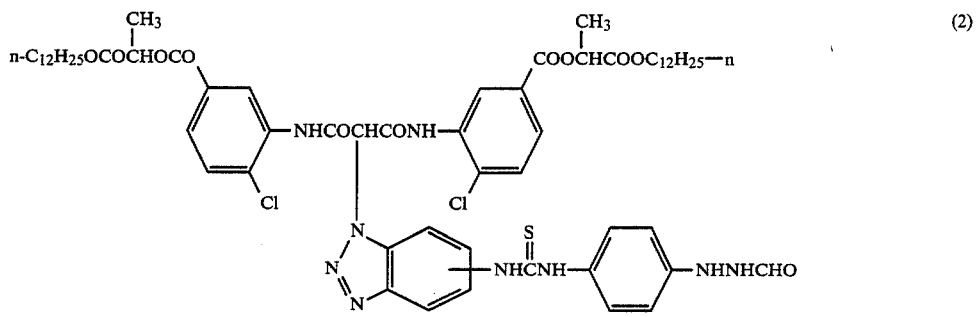
(2)
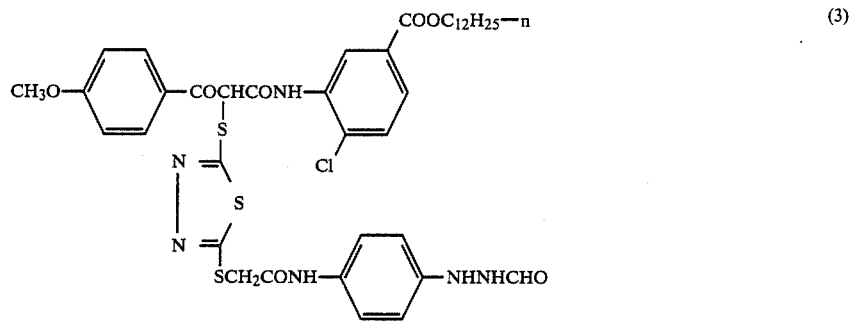
(3)

-continued
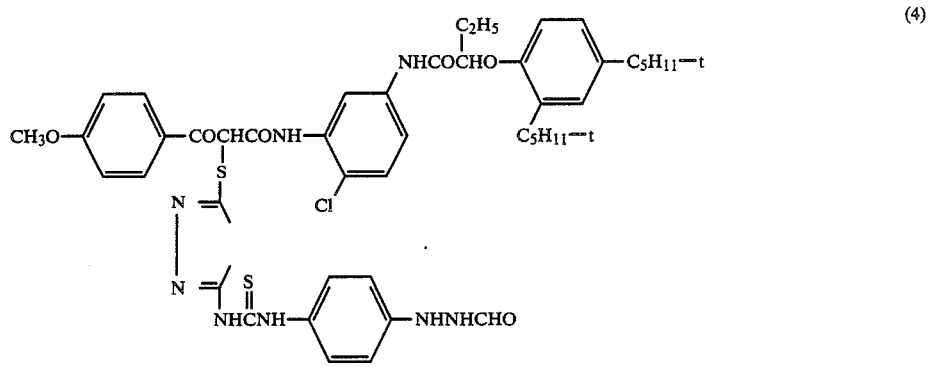
(4)
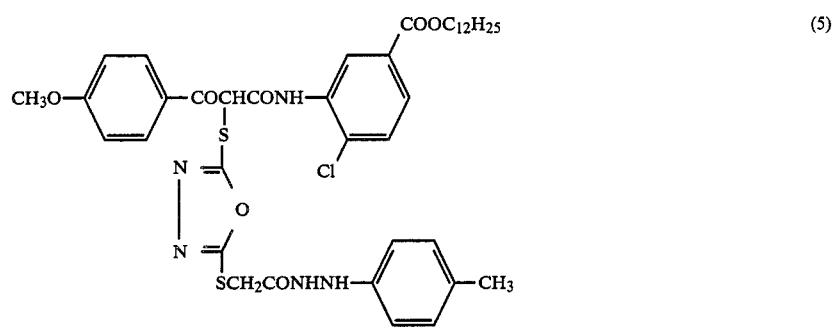
(5)
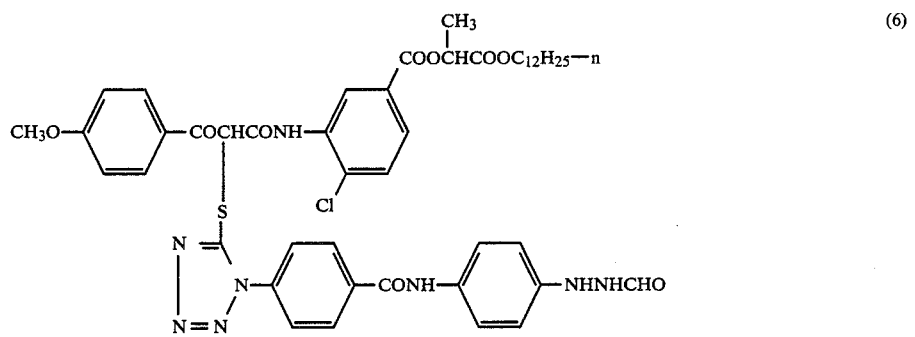
(6)
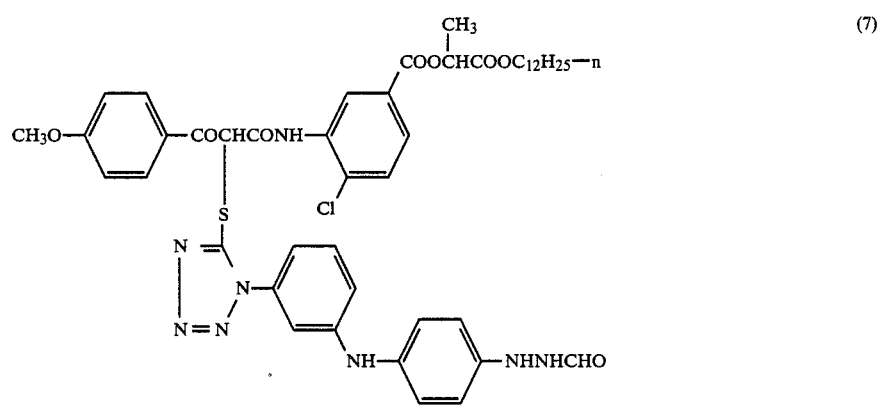
(7)

-continued
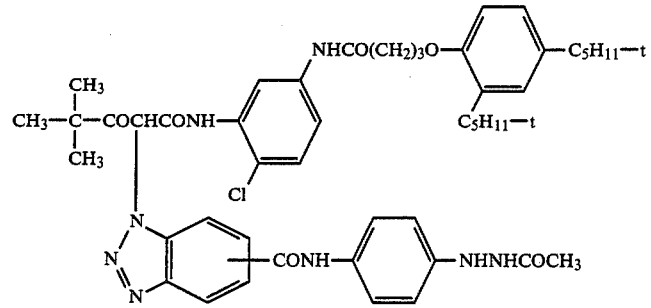
(8)
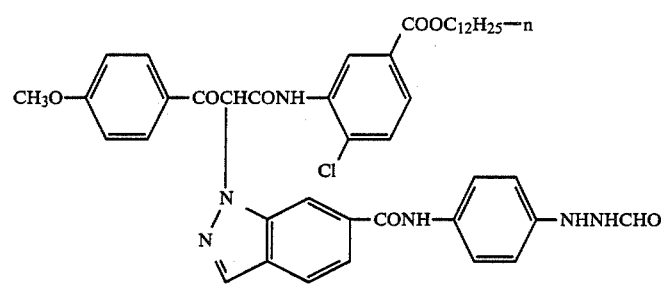
(9)
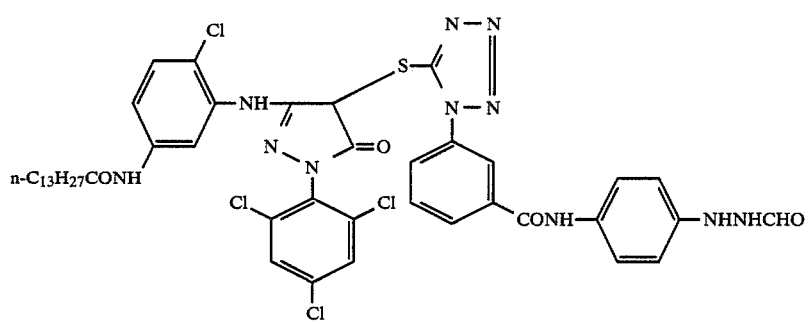
(10)
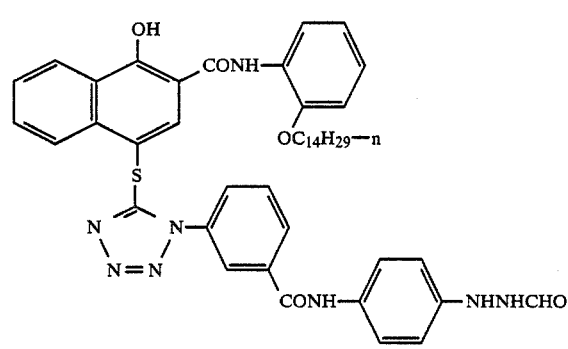
(11)

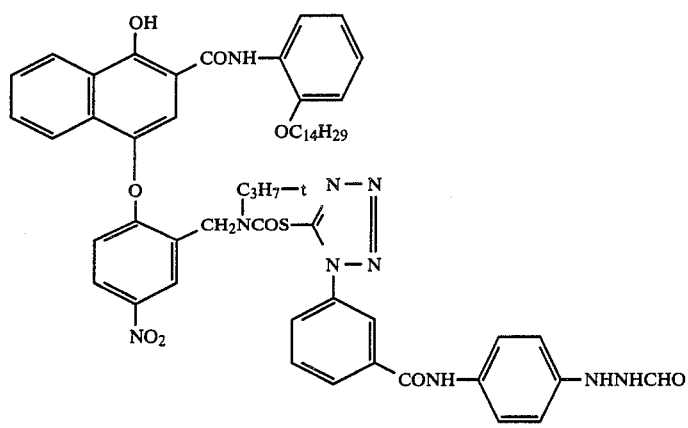
(12)
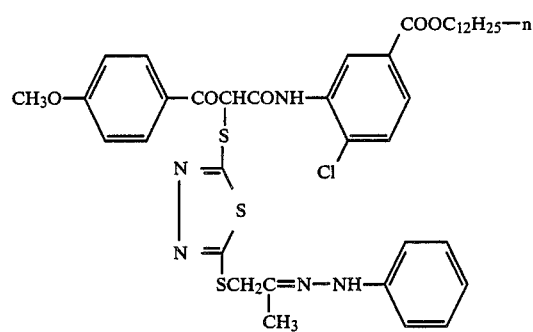
(13)
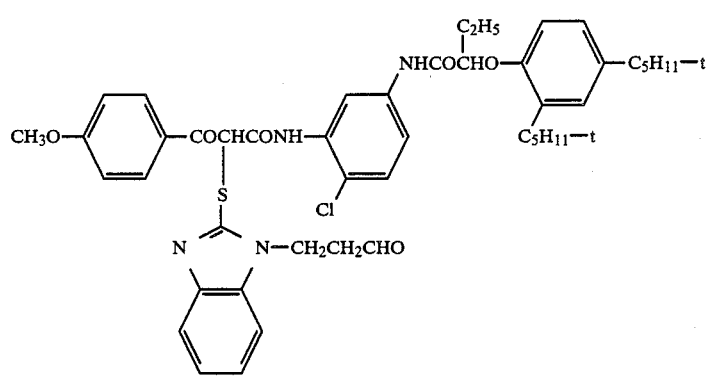
(14)
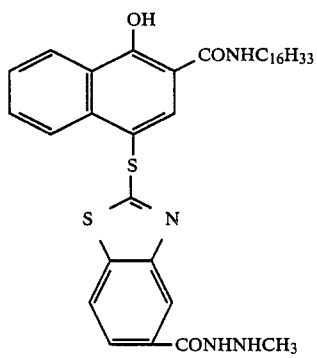
(15)
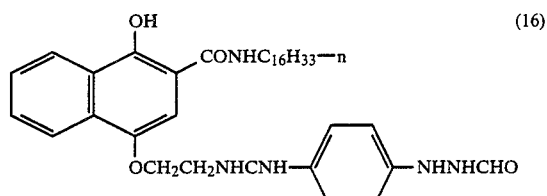
(16)

-continued
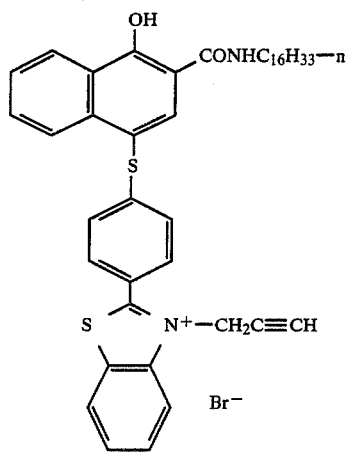 (17)
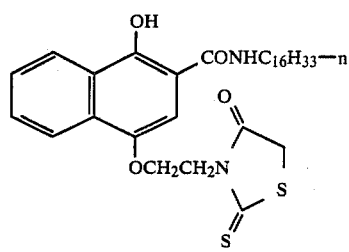 (18)
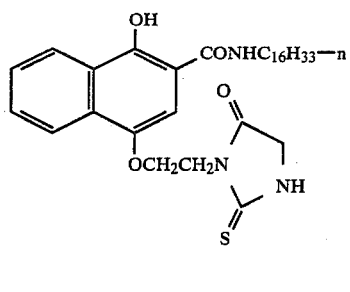 (19)
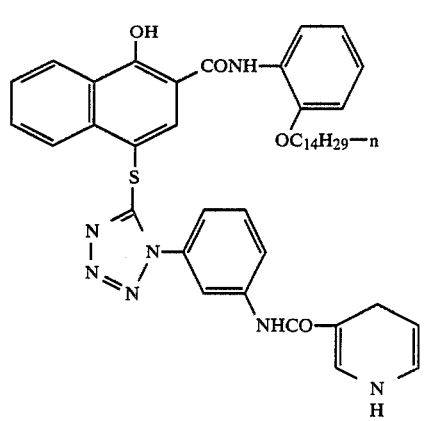 (20)
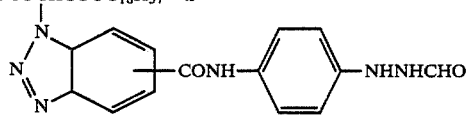 (21)
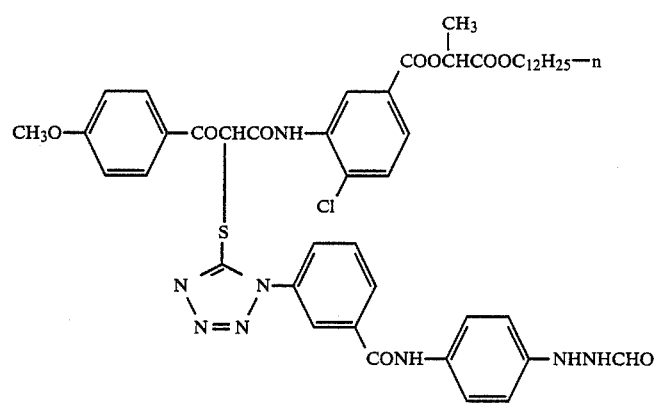 (22)

-continued
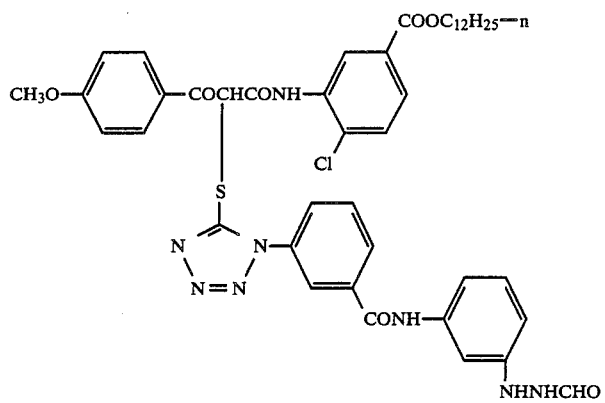
(23)
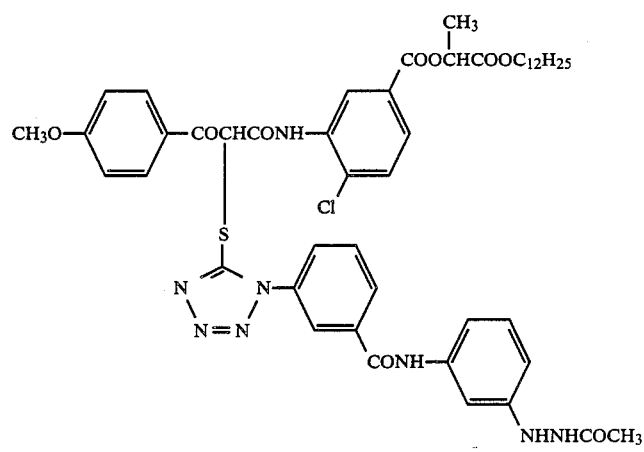
(24)
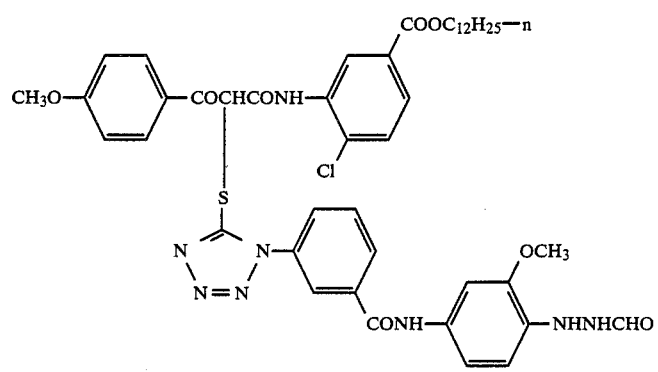
(25)
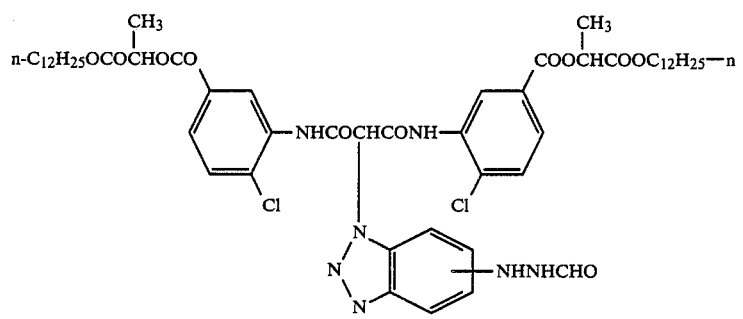
(26)

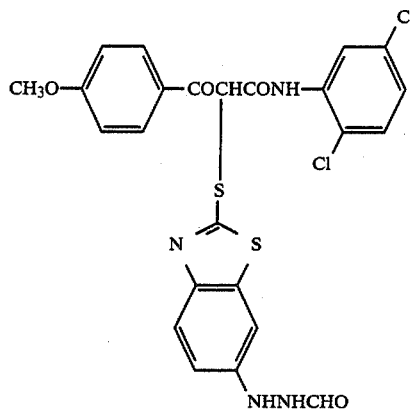
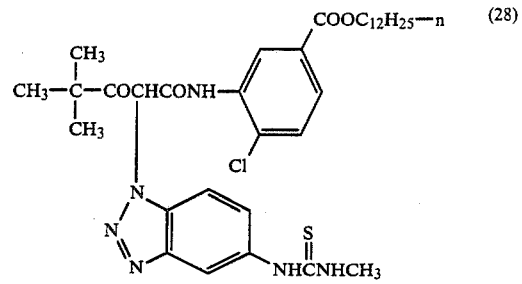

The compounds of the invention can be prepared by, for example, the synthesis route described in Japanese Patent Application (OPI) No. 150845/82. Some preparation examples are given below.

PREPARATION EXAMPLE 1

Synthesis of Compound (10)

A mixture of 15.4 g of 3-(2-chloro-5-tetradecaneamidoanilino)-1-(2,4,6-trichlorophenyl)-2-pyrazolin-5-one and 5.4 g of 1-(3-carboxyphenyl)-5-mercaptotetrazole was dissolved in 100 ml of dimethylformamide (DMF), and a solution of 4.9 g of N-glucosuccinic acid imide in 20 ml of DMF was added dropwise thereto at room temperature. The resulting mixture was stirred for 30 minutes, and 500 ml of water was added thereto. The mixture was then extracted with ethyl acetate. The ethyl acetate was distilled away under reduced pressure, and the residue was precipitated from a mixed solvent of ethyl acetate and acetonitrile to obtain 14 g of 3-(2-chloro-5-tetradecaneamidoanilino)-1-(2,4,6-trichlorophenyl)-4-[1-(3-carboxyphenyl)-5-tetrazolylthio]-2-pyrazolin-5-one, m.p., 155°–165° C. Yield was 68%.

A mixture of 8.3 g of 3-(2-chloro-5-tetradecaneamidoanilino)-1-(2,4,6-trichlorophenyl)-4-[1-(3-carboxyphenyl)-5-tetrazolylthio]-2-pyrazolin-5-one and 1.66 g of 1-formyl-2-(4-aminophenyl)hydrazine was dissolved in 50 ml of DMF, and a solution of 2.1 g of dicyclohexylcarbodiimide in 5 ml of DMF was added dropwise thereto at room temperature. The mixture was stirred at room temperature for 2 hours and filtered to remove dicyclohexylurea formed. To the filtrate was added 200 ml of water. Crystals precipitated were collected by filtration and recrystallized from a mixed solvent of ethyl acetate and methanol to obtain 5.6 g of the desired Compound (10), m.p., 175°–181° C. Yield was 58%.

| Elemental Analysis: | H (%) | C (%) | N (%) |
|---|---|---|---|
| Calculated for $C_{44}H_{47}N_{11}O_4SCl_4$ | 4.90 | 54.61 | 15.92 |
| Found | 4.94 | 54.44 | 15.88 |

PREPARATION EXAMPLE 2

Synthesis of Compound (11)

2-(2-Tetradecyloxyphenyl)carbamoyl-1-naphthol (22.8 g) was dissolved in 100 ml of dichloromethane, and a dichloromethane solution of sulphenyl chloride prepared from 25 g of 1-(3-ethoxycarbonylphenyl)-5-mercaptotetrazole and 13.5 g of sulfuryl chloride was added dropwise thereto at room temperature. The resulting dichloromethane solution was stirred for an additional 5 hours, and washed with an aqueous sodium bicarbonate solution and further with water. The dichloromethane was distilled away under reduced pressure and the residue was crystallized from methanol to obtain 26.9 g of 2-(2-tetradecyloxyphenyl)carbamoyl-4-[1-(3-ethoxycarbonylphenyl)-5-tetrazolylthio]-1-naphthol, m.p., 88°–90° C. Yield was 74.3%.

2-(2-Tetradecyloxyphenyl)carbamoyl-4-[1-(3-ethoxycarbonylphenyl)-5-tetrazolylthio]-1-naphthol (19.5 g) was added to a solution of 5.3 g of potassium hydroxide in 50 ml of methanol and stirred for 30 minutes at 40°–50° C. Then 10 ml of concentrated hydrochloric acid was diluted with 500 ml of water and poured into the reaction solution. Crystals precipitated were collected by filtration and recrystallized from methanol to obtain 16.1 g of 2-(2-tetradecyloxyphenyl)carbamoyl-4-[1-(3-carboxyphenyl)-5-tetrazolylthio]-1-naphthol, m.p., 136°–138° C. Yield was 86%.

A mixture of 13.9 g of 2-(2-tetradecyloxyphenyl)-carbamoyl-4-[1-(3-carboxyphenyl)-5-tetrazolylthio]-1-naphthol and 3.0 g of 1-formyl-2-(4-aminophenyl)hydrazine was dissolved in 20 ml of dimethylformamide (DMF), and a solution of 4.1 g of dicyclohexylcarbodiimide in 5 ml of DMF was added dropwise thereto in a nitrogen atmosphere while stirring at 0° C. The mixture was stirred for an additional 2 hours and then 2 hours at room temperature, and was filtered to remove dicyclohexylurea formed. The filtrate was poured into 1,500 ml of water. Crystals precipitated were collected by filtration and dissolved in 50 ml of DMF. The resulting DMF solution was treated with activated carbon and poured into 400 ml of methanol. Crystals precipitated were collected by filtration to obtain 9.2 g of the desired Compound (11), m.p., 173°–180° C. Yield was 55.5%.

| Elemental Analysis: | H (%) | C (%) | N (%) |
|---|---|---|---|
| Calculated for $C_{46}H_{52}N_8O_5S$ | 6.32 | 66.64 | 13.51 |
| Found | 6.27 | 66.53 | 13.35 |

An adsorbent (non-diffusing) foggant or development accelerator released from the compound of the invention in its coupling reaction with an oxidized developing agent starts development by fogging undeveloped silver halide grains, or accelerates development of silver halide grains which are slow in development. Thus the use of the compound of the invention offers various advantages.

(1) Comparing at the same exposure amount, the compound of the invention increases the density compared with conventional couplers.

(2) This increase in density is small because the amount of foggant released at fogging areas is small.

(3) The rate of development is increased.

These effects can be obtained by using the compound of the invention in only a very small amount. Furthermore, the compound of the invention does not move into other light-sensitive layers because of the presence of an absorbent group, and since the diffusibility of the compound of the invention is low, it does not enlarge the dye cloud, or reduce granularity. Hence the compound of the invention further has the following advantages.

(4) Color mixing does not occur.

(5) Graininess is good.

Addition of a very small amount of coupler, therefore, provides high sensitivity and gradation of high contrast in the present invention. This gradation of high contrast evidences that the forggant acts imagewise. In view of the high sensitivity and gradient of high contrast, the compound of the invention is effective for further improving image quality, particularly graininess when used in combination with a finely divided emulsion of low sensitivity, a low activity coupler, a development-inhibiting substance, or with a development inhibitor precursor.

The effects of the present invention as described above can be obtained if the compound of the invention is added in an amount of 1 mol% of all the couplers contained in an emulsion layer in which the compound of the invention is incorporated and other emulsion layers showing sensitivity to the same color as does the above emulsion layer. If the compound is added in an amount of not more than 0.6 mol%, the formation of fog can be reduced and also the gradation can be increased while maintaining the development accelerating effect at a high level. More preferably the compound of the invention is added in an amount of not more than 0.2 mol%.

The amount of the compound of the invention being added is not critical as long as the above-described effects of the present invention can be obtained. It is preferably not less than $5 \times 10^{-4}$ mol%.

The compound of the invention is sufficient to be added in a trace amount. It can be added to any of a cyan coupler-containing layer, a magenta coupler-containing layer, and a yellow coupler-containing layer without causing unfavorable side effects.

An increased rate of development, which is as described above one of the advantage of the invention, is useful in that the photographic processing can be performed quickly. Thus the compound of the invention exhibits a remarkable development accelerating action particularly when it is used in a multi-layer color light-sensitive material, since as well known in the art the development of such a multi-layer color light-sensitive material is slowed down by a delay in permeation of the developer into the lower layer portion and by diffusion of a development inhibiting substance from the upper layer portion.

The compound of the invention has an effect of greatly reducing the amount of "dead grains", i.e., silver halide grains which cannot be developed even if development is performed for a sufficiently long period. Hence, if the compound of the invention is incorporated in a color light-sensitive material in which a large amount of silver is used, the amount of silver used can be greatly reduced.

The compound of the invention can be used in ordinary silver halide color light-sensitive materials such as a color negative film, a color paper, a color positive film, a slide color reversal film, a movie color reversal film, and a TV color reversal film. In particular, it is effective for use in a color negative film and a color reversal film for which high sensitivity and high image quality are required.

Because of a recent steep rise in the price of silver, a reduction in the amount of silver to be used in light-sensitive materials is the most significant subject for those engaged in the field of photography. In view of this situation, it has been proposed to convert an X-ray film requiring a large amount of silver in the preparation thereof into a dye utilization type film. For example, the black color-forming coupler system is disclosed in U.S. Pat. Nos. 3,622,629, 3,734,735, 4,126,461, Japanese Patent Application (OPI) Nos. 42725/77, 105247/80, and 105248/80, and the three color mixing system as disclosed in *Research Disclosure*, RD-17123. Hence, in such light-sensitive materials requiring a large amount of silver in the preparation thereof, the compound of the invention can be effectively used since if the compound is used, silver halide is thoroughly utilized and the photographic processing can be performed quickly.

The compound of the invention can be incorporated in a silver halide emulsion layer by known techniques, such as the method described in U.S. Pat. No. 2,322,027. For example, the compound is dissolved in alkyl phthalates (e.g., dibutyl phthalate and dioctyl phthalate), phosphates (e.g., diphenyl phosphate, triphenyl phosphate, tricresyl phosphate, and dioctylbutyl phosphate), citrates (e.g., tributyl acetylcitrate), benzoates (e.g., octyl benzoate), alkylamides (e.g., diethyllaurylamide), fatty acid esters (e.g., dibutoxyethyl succinate and dioctyl azelate), trimesicates (e.g., tributyl trimesicate), etc., or organic solvents having a boiling point ranging between about 30° and 150° C., e.g., lower alkyl acetates such as ethyl acetate and butyl acetate, ethyl propionate, sec-butyl alcohol, methyl isobutyl ketone, $\beta$-ethoxyethyl acetate, and methyl cellosolve acetate and, thereafter, dispersed in hydrophilic colloid. The above-described high boiling and low boiling organic solvents can be used in combination with each other.

In addition, the dispersion method utilizing polymers as described in Japanese Patent Publication No. 39853/76 and Japanese Patent Application (OPI) No. 59943/76 can be used.

When the compound of the invention has acid groups such as carboxylic acid and sulfonic acid, it is introduced in the hydrophilic colloid as an alkaline aqueous solution.

In the preparation of the light-sensitive material of the invention, any of silver bromide, silver iodobromide, silver iodochlorobromide, silver chlorobromide and silver chloride can be used as silver halide. A preferred example is silver iodobromide.

Photographic emulsions which are used in the present invention may be subjected to spectral sensitization utilizing methine dyes, for example. These sensitizing dyes may be used singly or in combination with each other. Combinations of sensitizing dyes are often used for the purpose of super sensitization. In combination with such sensitizing dyes, dyes not having a sensitization action by themselves or substances not substantially absorbing visible light but showing super sensitization may be incorporated.

Useful sensitization dyes, combinations of dyes showing super sensitization, and substances showing super sensitization are described in *Research Disclosure*, Vol. 176, 17643 (December, 1978), page 23, IV-J.

The light-sensitive material of the invention may contain water-soluble dye as filter dye or for various purposes of, e.g., prevention of irradiation in the hydrophilic colloid layer thereof. Useful examples of such dyes include oxonol dye, hemioxonol dye, styryl dye, merocyanine dye, cyanine dye, and azo dye. Particularly preferred are oxonol dye, hemioxonol dye, and merocyanine dye.

In the light-sensitive material of the invention, the photographic emulsion layer may contain therein polyalkylene oxide or its derivatives such as ethers, esters and amines, thioether compounds, thiomorpholines, quaternary ammonium salt compounds, urethane derivatives, urea derivatives, imidazole derivatives, 3-pyrazolidone derivatives, etc. for the purposes of increasing sensitivity and contrast, or of accelerating development. For example, the compounds described in U.S. Pat. Nos. 2,400,532, 2,423,549, 2,716,062, 3,617,280, 3,772,021, 3,808,003, and British Pat. No. 1,488,991 can be used.

In photographic emulsions which are used in the present invention may be incorporated various compounds for the purpose of preventing fog during the preparation, storage or photographic processing of the light-sensitive material, or of stabilizing the photographic performance of the light-sensitive material. A number of compounds known as antifoggants or stabilizers, for example, azoles such as benzothiazolium salts, nitroindazoles, triazoles, benzotriazoles, and benzimidazoles (particularly nitro- or halogen-substituted products); heterocyclic mercapto compounds such as mercaptothiazoles, mercaptobenzothiazoles, mercaptobenzimidazoles, mercaptothiadiazoles, mercaptotetrazoles (particularly 1-phenyl-5-mercaptotetrazole), and mercaptopyrimidine; the above-described heterocyclic compounds further containing water-soluble groups such as a carboxyl group and a sulfonic group; thioketo compounds such as oxazolinethione; azaindenes such as tetrazaindenes (particularly 4-hydroxy-substituted (1,3,3a,7)tetrazaindenes); benzenethiosulfonic acids; and benzenesulfinic acid can be added.

The light-sensitive material of the invention may contain compounds such as hydroquinone derivatives, aminophenol derivatives, gallic acid derivatives, and ascorbic acid derivatives as color antifoggants.

In the practice of the invention, the known antifading agents as described below can be used in combination. These antifading agents include hydroquinone derivatives, gallic acid derivatives, p-alkoxyphenols, p-oxyphenol derivatives, and bisphenols. Color image stabilizers can be used singly or in combination with each other.

The light-sensitive material of the invention may contain an ultraviolet absorber in its hydrophilic colloid layer. Ultraviolet absorbers which can be used include benzotriazole compounds substituted by an aryl group, 4-thiazolidone compounds, benzophenone compounds, cinnamate compounds, butadiene compounds, benzoxazole compound, and the like. In addition, ultraviolet absorbing polymers can be used. These ultraviolet absorbers may be fixed in the above-described hydrophilic colloid layer.

The present invention is described in greater detail with reference to the following examples. However, the scope of the invention is not limited to the examples.

EXAMPLE I

Emulsion and protective layers having the formulations as described hereinafter were provided on a cellulose triacetate film support coated with a subbing layer. In preparing the emulsion, a compound of the invention or comparative compound as shown in Table 1 was dissolved in tricresyl phosphate and ethyl acetate in combination with Yellow Coupler (C-1) and emulsified in an aqueous gelatin solution.

| | Amount |
|---|---|
| Emulsion Layer | |
| Negative type silver iodobromide emulsion (grain size: 1.0μ) | $7.5 \times 10^{-3}$ mole/m$^2$ (calculated as silver) |
| Yellow Coupler | $7.5 \times 10^{-4}$ mole/m$^2$ |
| Compound of the invention or comparative compound | Shown in Table 1 |
| Tricresyl phosphate | 0.4 g/m$^2$ |
| Gelatin | 1.6 g/m$^2$ |
| Protective Layer | |
| Gelatin | $1.30 \times 10$ g/m$^2$ |
| Hardener H-1 | 0.05 g/m$^2$ |

The thus prepared light-sensitive materials were allowed to stand for 14 hours at 40° C. and 10% relative humidity. At the end of the time, the materials were exposed to white light for sensitometry and then processed at 38° C. as follows.

| | Time (min) |
|---|---|
| 1. Color development | 3.25 |
| 2. Bleach | 6.5 |
| 3. Rinsing | 3.25 |
| 4. Fixing | 6.5 |
| 5. Rinsing | 3.25 |
| 6. Stabilization | 3.25 |

The composition of each processing solution is shown below.

| | Amount |
|---|---|
| Color Developer | (g) |
| Sodium nitrotriacetate | 1.0 |
| Sodium sulfite | 4.0 |
| Sodium carbonate | 30.0 |
| Potassium bromide | 1.4 |
| Hydroxylamine sulfate | 2.4 |
| 4-(N—Ethyl-N—β-hydroxyethylamino)-2-methylaniline sulfate | 4.5 |
| Water to make | 1,000 ml |
| Bleaching Solution | |
| Ammonium bromide | 160.0 g |
| Ammonia water (28%) | 25.0 ml |
| Sodium iron ethylenediaminetetraacetate | 130 g |
| Glacial acetic acid | 14 ml |
| Water to make | 1,000 ml |
| Fixing Solution | |
| Sodium tetrapolyphosphate | 2.0 g |
| Sodium sulfite | 4.0 g |
| Ammonium thiosulfate (70%) | 175.0 ml |
| Sodium hydrogensulfite | 4.6 g |
| Water to make | 1,000 ml |

-continued

| | Amount |
|---|---|
| Stabilizing Solution | |
| Formalin | 8.0 ml |
| Water to make | 1,000 ml |

The density of each material was measured using blue light. The results are shown in Table 1.

TABLE 1

| Run No. | Compound Type | Amount* | Fog | Gamma | Relative Sensitivity** |
|---|---|---|---|---|---|
| 1 (Control) | — | — | 0.13 | 1.21 | 100 |
| 2 (Comparative Example) | C-2 | 20 | 0.13 | 1.33 | 123 |
| 3 (Comparative Example) | C-2 | 2 | 0.12 | 1.21 | 100 |
| 4 (Comparative Example) | C-3 | 20 | 0.14 | 1.30 | 123 |
| 5 (Comparative Example) | C-3 | 2 | 0.13 | 1.22 | 100 |
| 6 (Comparative Example) | (3) | 1.2 | 0.28 | 1.20 | 120 |
| 7 (Example of the invention) | (3) | 0.6 | 0.18 | 1.25 | 130 |
| 8 (Example of the invention) | (3) | 0.06 | 0.13 | 1.33 | 139 |
| 9 (Example of the invention) | (1) | 0.10 | 0.14 | 1.39 | 159 |
| 10 (Example of the invention) | (18) | 0.06 | 0.14 | 1.34 | 130 |
| 11 (Example of the invention) | (19) | 0.06 | 0.13 | 1.31 | 132 |
| 12 (Example of the invention) | (22) | 0.06 | 0.13 | 1.35 | 145 |

*Amount of Compound added indicated in terms of mol percent based on C-1.
**Relative Sensitivity: Reciprocal of an exposure amount providing a color density of fog +0.2 and indicated as a relative value with that of Control as 100.

It can be seen from Table 1 that in Run Nos. 2 to 4 in which Comparative Compounds C-2 and C-3 are used, if the amount of Yellow Coupler C-1 is not more than 1 mol%, almost no effects in terms of high sensitivity and high contrast can be obtained, whereas if the compound of the invention is incorporated in an amount of not more than 1 mol%, the sensitivity is increased and the contrast becomes high. On the other hand, if the amount is more than 1 mol% as in Run No. 6, the fog is seriously increased.

The structures of the comparative couplers and hardener as used herein are shown below.

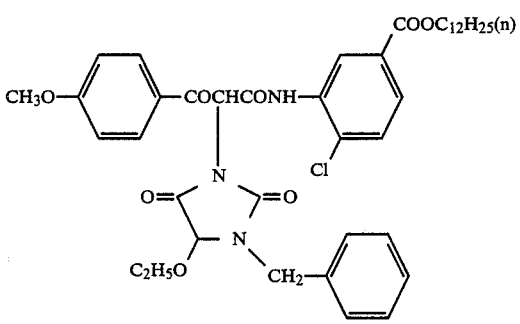

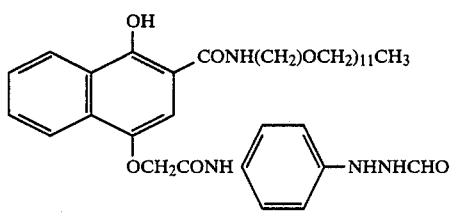

C-2

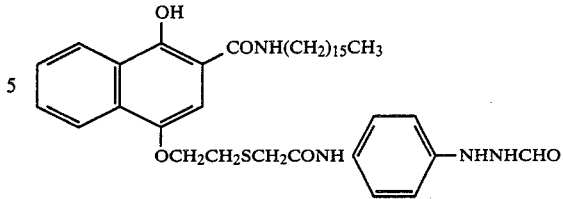

C-3

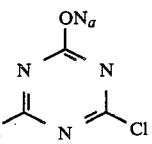

H-1

EXAMPLE 2

A multi-layer color light-sensitive material was prepared by providing the layers as described hereinafter on a cellulose triacetate film support. This material is referred to as Sample 201.

| First Layer (Antihalation Layer (AHL)) | |
|---|---|
| Gelatin layer containing black colloid silver | |
| Second Layer (Interlayer Layer (ML)) | |
| Gelatin layer containing an emulsion of 2,5-di-tert-octylhydroquinone. | |
| Third Layer (First Red-Sensitive Emulsion Layer (RL$_1$)) | |
| Silver iodobromide emulsion (silver iodide: 5 mol %, mean grain size: 0.5μ) | 1.90 g/m$^2$ (calculated as silver) |
| Sensitizing Dye I | 6 × 10$^{-5}$ mol per mol of silver |
| Sensitizing Dye II | 1.5 × 10$^{-5}$ mol per mol of silver |
| Coupler C-4 | 0.04 mol per mol of silver |
| Coupler C-5 | 0.003 mol per mol of silver |
| Coupler C-6 | 0.0006 mol per mol of silver |
| Fourth Layer (Second Red-Sensitive Emulsion Layer (RL$_2$)) | |
| Silver iodobromide emulsion (silver iodide: 8 mol %; mean grain size: 1.2μ) | 1.6 g/m$^2$ calculated as silver) |
| Sensitizing Dye I | 2.5 × 10$^{-5}$ mol per mol of silver |
| Sensitizing Dye II | 1.0 × 10$^{-5}$ mol per |

-continued

| | |
|---|---|
| Coupler C-7 | 0.02 mol per mol of silver |
| Coupler C-5 | 0.0016 mol per mol of silver |
| Fifth Layer (Interlayer Layer (ML)) | |
| Same as Second Layer. | |
| Sixth Layer (First Green-Sensitive Emulsion Layer (GL$_1$)) | |
| Silver iodobromide emulsion (silver iodide: 4 mol % mean grain size, 0.45 μ) | 1.6 g/m$^2$ (calculated as silver) |
| Sensitizing Dye III | $3 \times 10^{-5}$ mol per mol of silver |
| Sensitizing Dye IV | $1 \times 10^{-5}$ mol per mol of silver |
| Coupler C-8 | 0.05 mol per mol of silver |
| Coupler C-9 | 0.008 mol per mol of silver |
| Coupler C-6 | 0.0015 mol per mol of silver |
| Seventh Layer (Second Green-Sensitive Emulsion Layer (GL$_2$)) | |
| Silver iodobromide (silver iodide: 8 mol %; mean grain size: 0.9μ) | 1.8 g/m$^2$ (calculated as silver) |
| Sensitizing Dye III | $2.5 \times 10^{-5}$ mol per mol of silver |
| Sensitizing Dye IV | $0.8 \times 10^{-5}$ mol per mol of silver |
| Coupler C-10 | 0.003 mol per mol of silver |
| Coupler C-11 | 0.017 mol per mol of silver |
| Eighth Layer (Yellow Filter Layer (YFL)) | |
| Gelatin layer containing yellow colloid silver and an emulsion of 2,5-di-tert-octylhydroquinone. | |
| Nineth Layer (First Blue-Sensitive Layer (BL$_1$)) | |
| Silver iodobromide (silver iodide: 6 mol %; mean grain size: 0.5μ) | 1.6 g/m$^2$ (calculated as silver) |
| Coupler C-1 | 0.25 mol per mol of silver |
| Coupler C-6 | 0.015 mol per mol of silver |
| Tenth Layer (Second Blue-Sensitive Layer (BL$_2$)) | |
| Silver iodobromide (silver iodide: mean grain size: 1.0μ) | 1.1 g/m$^2$ (calculated as silver) |
| Coupler C-1 | 0.06 mol per mol of silver |
| Eleventh Layer (Protective Layer (PL)) | |
| Gelatin layer containing trimethyl methacrylate particles (diameter: 1.5μ) | |

As well as the above described composition, a gelatin hardener, H-1, and a surfactant were added to each layer.

In addition to Sample 201, Samples 202 to 209 were prepared as follows:

Preparation of Samples 202 and 203

Samples 202 and 203 were prepared in the same manner as in Sample 201 except that C-2 and C-3, respectively, were further added to BL$_1$ in an amount of 10 mol% based on Yellow Coupler C-1.

Preparation of Samples 204 to 209

Samples 204 to 209 were prepared in the same manner as in Sample 201 except that C-2, C-3, Compounds (6), (3), (18) and (19) of the invention, respectively, were further added to BL$_1$ in an amount of 0.03 mol% based on Yellow Coupler C-1.

Samples 201 to 209 were exposed to white light for sensitometry and then were subjected to the same color development as in Example 1. The density of each sample was measured using blue light. The results are shown in Table 2.

TABLE 2

| Run No. | | Compound Type | Amount* | Photographic Properties Minimum Density | Maximum Density |
|---|---|---|---|---|---|
| Sample 201 | (Control) | — | — | 0.52 | 100 |
| Sample 202 | (Comparative Example) | C-2 | 20 | 0.53 | 105 |
| Sample 203 | (Comparative Example) | C-3 | 20 | 0.54 | 103 |
| Sample 204 | (Comparative Example) | C-2 | 0.06 | 0.52 | 100 |
| Sample 205 | (Comparative Example) | C-3 | 0.06 | 0.51 | 98 |
| Sample 206 | (Example of the invention) | (3) | 0.06 | 0.53 | 125 |
| Sample 207 | (Example of the invention) | (18) | 0.06 | 0.53 | 120 |
| Sample 208 | (Example of the invention) | (19) | 0.06 | 0.54 | 118 |
| Sample 209 | (Example of the invention) | (22) | 0.06 | 0.52 | 125 |

Note:
*Amount of Compound added: Indicated in terms of mol percent based on C-1 contained in BL$_2$.

It can be seen from Table 2 that even if C-2 and C3 are each added in an amount of 10 mol% based on the main coupler, C-1, an increase in sensitivity is small and if they are added in an amount of 0.03 mol%, no effect can be obtained, whereas if the compounds of the invention are added only in an amount as small as 0.03 mol%, the sensitivity is greatly increased with almost no increase in fog.

The compounds used in preparing the above samples are as follows:

Sensitizing Dye I: Anhydro-5,5'-dichloro-3,3'-di-(γ-sulfopropyl)-9-ethylthiacarbocyanine hydroxide pyridinium salt Sensitizing Dye II: Anhydro-9-ethyl-3,3'-di-(γ-sulfopropyl)-4,5,4',5'-dibenzothiacarbocyanine hydroxide triethylamine salt Sensitizing Dye III: Anhydro-9-ethyl-5,5'-dichloro-3,3'-di-(γ-sulfopropyl)oxacarbocyanine sodium salt Sensitizing Dye IV: Anhydro-5,6,5',6'-tetrachloro-1,1'-diethyl-3,3'-di-{β-[β-(γ-sulfopropoxy)ethoxy]ethylimidazolocarbocyanine hydroxide sodium salt

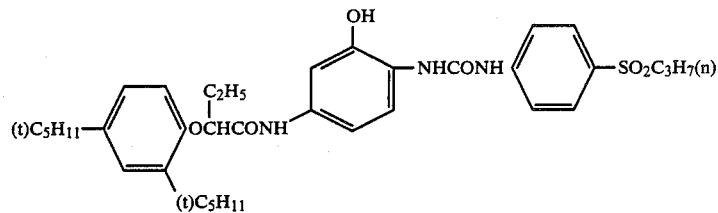
C-4
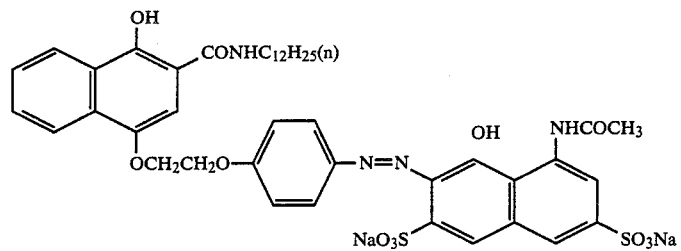
C-5
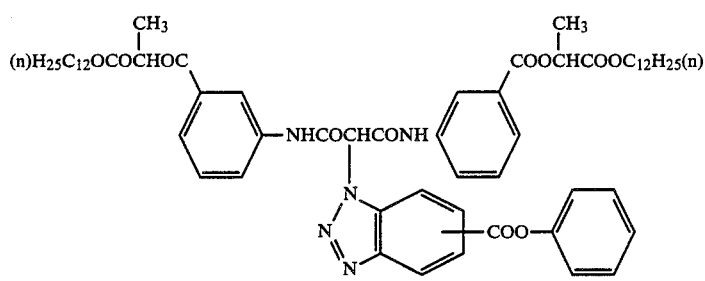
C-6
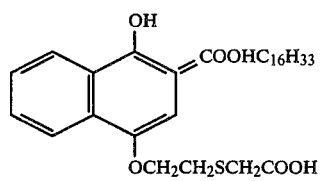
C-7
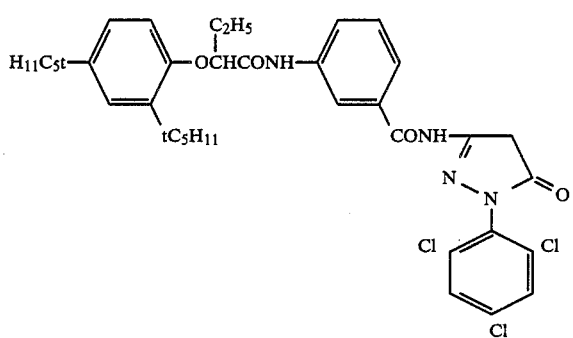
C-8
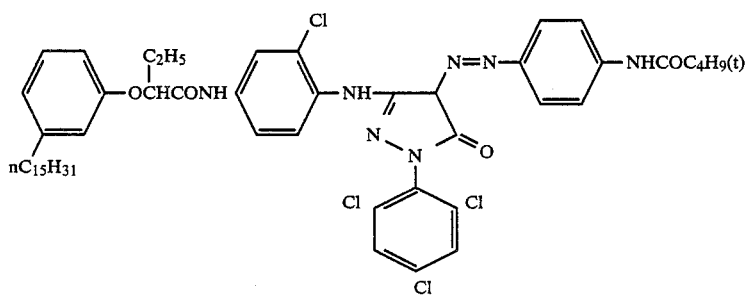
C-9

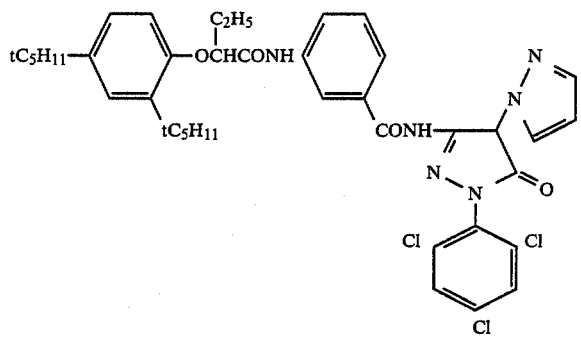

C-10

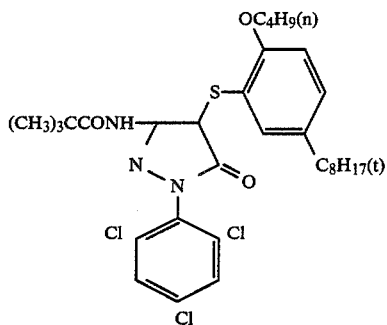

C-11

While the invention has been described in detail and with reference to specific embodiments thereof, it will be apparent to one skilled in the art that various changes and modifications can be made therein without departing from the spirit and scope thereof.

What is claimed is:

1. A silver halide color light-sensitive material comprising a support and a light-sensitive silver halide emulsion layer on the support, wherein a compound represented by the general formula (I):

$$\text{Coup}-(\text{TIME})_n-\text{FA} \quad (I)$$

wherein Coup represents a coupler radical capable of undergoing a coupling reaction with an oxidized product of an aromatic primary amine developing agent; TIME represents a timing group which is eliminated from Coup by the coupling reaction and, thereafter, releases FA; n is 0 or 1; and FA represents a group which is eliminated from Coup in the coupling reaction when n is 0, whereas FA is released from TIME when n is 1, and FA has adsorption properties with respect to silver halide grains and also has a substantial fogging action with respect to silver halide grains, is incorporated in the light-sensitive silver halide emulsion layer in an amount of not more than 1 mol% based on all couplers contained in said emulsion layer and other emulsion layer sensitive to the same color as said emulsion layer.

2. A silver halide color light-sensitive material as claimed in claim 1, wherein FA is represented by the formula, $$\text{AD}-(\text{L})_m-\text{X}$$

wherein AD is a group capable of being adsorbed onto silver halide grains, L is a divalent bonding group, X is a reducing group, or a group capable of forming silver sulfide at the time of development, and m is 0 or 1.

3. A silver halide color lignt-sensitive material as claimed in claim 1, wherein the compound represented by the general formula (I) is present in an amount in the range of $5\times 10^{-4}$ mol% to 1 mol% based on all couplers contained in the emulsion layer and other emulsion layers sensitive to the same color as the emulsion layer.

4. A silver halide color light-sensitive material as claimed in claim 3, wherein the compound represented by the general formula (I) is present in an amount in the range of $5\times 10^{-4}$ mol% to 0.6 mol% based on all couplers contained in the emulsion layer and other emulsion layer sensitive to the same color as the emulsion layer.

5. A silver halide color light-sensitive material as claimed in claim 4, wherein the compound represented by the general formula (I) is present in an amount in the range of $5\times 10^{-4}$ mol% to 0.2 mol% based on all couplers contained in the emulsion layer and other emulsion layers sensitive to the same color as the emulsion layer.

6. A method of producing an image in a silver halide color light-sensitive material, comprising:
imagewise exposing and developing a silver halide color light-sensitive material comprising a support and a light-sensitive silver halide emulsion layer on said support,
said silver halide emulsion layer containing a compound represented by the general formula (I):

$$\text{Coup}-(\text{TIME})_n-\text{FA}$$

wherein Coup represents a coupler radical capable of undergoing a coupling reaction with an oxidized product of an aromatic primary amine developing agent; TIME represents a timing group which is eliminated from Coup by the coupling reaction and, thereafter, releases FA; n is 0 or 1; FA represents a group which is eliminated from Coup in the coupling reaction when n is 0, whereas FA is released from TIME when n is 1, and FA has adsorption properties with respect to silver halide grains and also has a substantial fogging action with respect to silver halide grains; and said compound represented by the general formula (I) being incorporated in the light-sensitive halide emulsion layer in an amount of not more than 1 mol% based on all couplers contained in said emulsion layer and in other emulsion layers sensitive to the same color as said emulsion layer.

7. A silver halide color light-sensitive material as claimed in claim 2, wherein X is a hydrazide.

8. A silver halide color light-sensitive material is claimed in claim 2, wherein L is a divalent bonding group selected from the group consisting of alkylene, alkenylene, phenylene, naphthylene, —O—, —S—, —SO—, —SO$_2$—, carbonylamido, thioamido, sulfonamido, ureido, thiouredio and heterocyclic rings.

9. A silver halide color light-sensitive material is claimed in claim 1, wherein n is 0.

10. A silver halide color light-sensitive material is claimed in claim 1, wherein n is 1.

11. A silver halide color light-sensitive material is claimed in claim 2, wherein m is 0.

12. A silver halide color light-sensitive material is claimed in claim 2, wherein m is 1.

* * * * *